(12) United States Patent
Balakrishnan et al.

(10) Patent No.: US 10,900,992 B2
(45) Date of Patent: *Jan. 26, 2021

(54) CALCULATING PACE AND ENERGY EXPENDITURE FROM ATHLETIC MOVEMENT ATTRIBUTES

(71) Applicant: NIKE, Inc., Beaverton, OR (US)

(72) Inventors: Santoshkumar Balakrishnan, Portland, OR (US); Manan Goel, Beaverton, OR (US); Bradley W. Wilkins, Beaverton, OR (US); Corey Dow-Hygelund, Sunriver, OR (US); Jeff Hazel, Bend, OR (US); John Schmitt, Bend, OR (US)

(73) Assignee: NIKE, Inc., Beaverton, OR (US)

( * ) Notice: Subject to any disclaimer, the term of this patent is extended or adjusted under 35 U.S.C. 154(b) by 466 days.

This patent is subject to a terminal disclaimer.

(21) Appl. No.: 14/514,049

(22) Filed: Oct. 14, 2014

(65) Prior Publication Data
US 2016/0045159 A1    Feb. 18, 2016

Related U.S. Application Data

(60) Provisional application No. 61/900,203, filed on Nov. 5, 2013, provisional application No. 61/890,748, filed on Oct. 14, 2013.

(51) Int. Cl.
| | |
|---|---|
| *G01P 13/00* | (2006.01) |
| *G01B 21/00* | (2006.01) |
| *G01P 15/00* | (2006.01) |
| *G06N 20/00* | (2019.01) |
| *A61B 5/00* | (2006.01) |
| *A61B 5/0205* | (2006.01) |
| *A61B 5/024* | (2006.01) |
| *A61B 5/11* | (2006.01) |
| *G16H 40/67* | (2018.01) |
| *G06F 3/01* | (2006.01) |
| *G06K 9/00* | (2006.01) |
| *G01P 15/18* | (2013.01) |
| *A63B 24/00* | (2006.01) |

(Continued)

(52) U.S. Cl.
CPC ............ *G01P 13/00* (2013.01); *A61B 5/0022* (2013.01); *A61B 5/024* (2013.01); *A61B 5/0205* (2013.01); *A61B 5/02438* (2013.01); *A61B 5/1118* (2013.01); *A61B 5/1123* (2013.01); *A61B 5/4866* (2013.01); *A61B 5/6823* (2013.01); *A61B 5/7235* (2013.01); *A61B 5/7246* (2013.01); *A61B 5/7278* (2013.01); *A63B 24/0006* (2013.01); *A63B 24/0062* (2013.01); *G01B 21/00* (2013.01); *G01P 15/00* (2013.01); *G01P 15/18* (2013.01); *G06F 1/163* (2013.01); *G06F 3/011* (2013.01); *G06F 3/014* (2013.01); *G06F 3/017* (2013.01); *G06K 9/00348* (2013.01); *G06K 9/00543* (2013.01); *G06N 5/04* (2013.01); *G06N 20/00* (2019.01); *G16H 40/67* (2018.01); *A61B 5/002* (2013.01); *A61B 5/0024* (2013.01); *A61B 5/0059* (2013.01); *A61B 5/01* (2013.01); *A61B 5/0833* (2013.01); *A61B 5/1112* (2013.01); *A61B 5/4806* (2013.01); *A61B 5/681* (2013.01); *A61B 5/6804* (2013.01); *A61B 5/6807* (2013.01); *A61B 5/6898* (2013.01); *A61B 2562/0219* (2013.01); *A61B 2562/0247* (2013.01); *A63B 2024/0015* (2013.01); *A63B 2024/0068* (2013.01); *A63B 2230/06* (2013.01); *G06F 19/3481* (2013.01); *G16H 20/30* (2018.01)

(58) Field of Classification Search
None
See application file for complete search history.

(56) References Cited

U.S. PATENT DOCUMENTS

| | | |
|---|---|---|
| 5,598,849 A | 2/1997 | Browne |
| 6,624,802 B1 | 9/2003 | Klein et al. |

(Continued)

FOREIGN PATENT DOCUMENTS

| | | |
|---|---|---|
| JP | 2002263086 A | 9/2002 |
| JP | 2005034364 A | 2/2005 |

(Continued)

OTHER PUBLICATIONS

J.Staudenmayer et al: "An Artificial neural network to estimate physical activity energy expenditure and identify physical activity type from an accelerometer", Journal of Applied Physiology, vol. 107, No. 4, Jul. 30, 2009.

(Continued)

*Primary Examiner* — G Steven Vanni
(74) *Attorney, Agent, or Firm* — Banner & Witcoff, Ltd.

(57) ABSTRACT

Systems and methods configured to process motion data associated with a user. The systems and methods are configured to receive motion data from a sensor, calculate motion attributes from the data, and classify the motion data using one or more mathematical models. Attributes may be calculated without classifying the motion data into an activity type (such as walking, running, swimming, or any specific or general activity). Attributes may be compared to activity models comprising motion data from several individuals, which may not include the user. Motion data within the models and attributes of the user may be independent of any activity type. Attributes may be compared to select an energy expenditure model from one or more energy expenditure models, which may be selected as a best-match to the one or more motion attributes. An energy expenditure associated with the motion of the user may then be calculated.

21 Claims, 29 Drawing Sheets

(51) Int. Cl.
  *G06F 1/16* (2006.01)
  *G06N 5/04* (2006.01)
  *G16H 20/30* (2018.01)
  *A61B 5/01* (2006.01)
  *A61B 5/083* (2006.01)
  *G06F 19/00* (2018.01)

(56) References Cited

U.S. PATENT DOCUMENTS

| | | |
|---|---|---|
| 7,198,607 B2 | 4/2007 | Jamsen |
| 7,653,508 B1 | 1/2010 | Kahn et al. |
| 7,818,131 B2 | 10/2010 | Mott |
| 8,478,542 B2 | 7/2013 | Mott |
| 8,671,784 B2 | 3/2014 | Nishibayashi |
| 8,747,336 B2 | 6/2014 | Tran |
| 8,852,097 B2 | 10/2014 | Shimada et al. |
| 8,892,481 B2 | 11/2014 | Landers |
| 9,017,257 B2 | 4/2015 | Kodama et al. |
| 9,665,873 B2 | 5/2017 | Ackland et al. |
| 2002/0156351 A1 | 10/2002 | Sagel |
| 2005/0171410 A1 | 8/2005 | Hjelt et al. |
| 2006/0004265 A1 | 1/2006 | Pulkkinen et al. |
| 2006/0015149 A1 | 1/2006 | Baker |
| 2006/0112754 A1 | 6/2006 | Yamamoto et al. |
| 2006/0161079 A1 | 7/2006 | Choi et al. |
| 2007/0010720 A1 | 1/2007 | Mott |
| 2007/0238938 A1 | 10/2007 | Nishibayashi et al. |
| 2007/0255154 A1 | 11/2007 | Lu et al. |
| 2007/0282176 A1 | 12/2007 | Shimada et al. |
| 2008/0167580 A1 | 7/2008 | Avni et al. |
| 2008/0275348 A1 | 11/2008 | Catt et al. |
| 2008/0281234 A1 | 11/2008 | Gods et al. |
| 2009/0163835 A1 | 6/2009 | Logan et al. |
| 2009/0221937 A1 | 9/2009 | Smith et al. |
| 2010/0096691 A1 | 4/2010 | Shin et al. |
| 2010/0121227 A1 | 5/2010 | Stirling et al. |
| 2010/0234693 A1 | 9/2010 | Srinivasan et al. |
| 2010/0256532 A1 | 10/2010 | Nishibayashi |
| 2011/0029250 A1 | 2/2011 | Mott |
| 2011/0046519 A1 | 2/2011 | Raheman |
| 2011/0054359 A1 | 3/2011 | Sazonov et al. |
| 2011/0152695 A1 | 6/2011 | Granqvist et al. |
| 2011/0288784 A1 | 11/2011 | Jangle et al. |
| 2012/0116177 A1 | 5/2012 | Lho et al. |
| 2012/0119126 A1 | 5/2012 | Choi |
| 2012/0316455 A1 | 12/2012 | Rahman et al. |
| 2012/0316456 A1 | 12/2012 | Rahman et al. |
| 2013/0053990 A1 | 2/2013 | Ackland |
| 2013/0173174 A1 | 7/2013 | Baxi |
| 2013/0191034 A1 | 7/2013 | Weast et al. |
| 2013/0324888 A1 | 12/2013 | Solinsky |
| 2014/0005575 A1 | 1/2014 | Ogawa et al. |
| 2014/0045150 A1 | 2/2014 | Kodama et al. |
| 2014/0249852 A1 | 9/2014 | Proud |
| 2014/0288448 A1 | 9/2014 | Saalasti et al. |
| 2014/0349256 A1 | 11/2014 | Connor |
| 2015/0057967 A1 | 2/2015 | Albinali |
| 2016/0045159 A1 | 2/2016 | Balakrishnan et al. |
| 2016/0196325 A1 | 7/2016 | Andon et al. |
| 2016/0196326 A1 | 7/2016 | Andon et al. |
| 2016/0213974 A1 | 7/2016 | Balakrishnan et al. |
| 2016/0223580 A1 | 8/2016 | Balakrishnan et al. |
| 2016/0256741 A1 | 9/2016 | Holma et al. |
| 2016/0346614 A1 | 12/2016 | Kirby et al. |

FOREIGN PATENT DOCUMENTS

| | | |
|---|---|---|
| JP | 2006192276 A | 7/2006 |
| JP | 2010096691 A | 4/2010 |
| JP | 2013109780 A | 6/2013 |
| KR | 100601981 B1 | 7/2006 |
| WO | 2010096691 A2 | 8/2010 |
| WO | 2012119126 A2 | 9/2012 |
| WO | 2012135767 A1 | 10/2012 |
| WO | 2012166416 A1 | 12/2012 |
| WO | 2013082436 A1 | 6/2013 |
| WO | 2013109780 A2 | 7/2013 |

OTHER PUBLICATIONS

Jan. 22, 2015—(WO) ISR and WO—App. No. PCT/US14/060480.
Jan. 22, 2015—(WO) ISR and WO—App. No. PCT/US14/060442.
S.E. Crouter et al: "A New 2-regression model for the Actical accelerometer", British Journal of Sports Medicine, vol. 42, No. 3, Mar. 1, 2008.
Jan. 29, 2015—(WO) ISR—App. No. PCT/US2014/02116.
Jan. 15, 2015—(WO) ISR—App. No. PCT/US201406044.

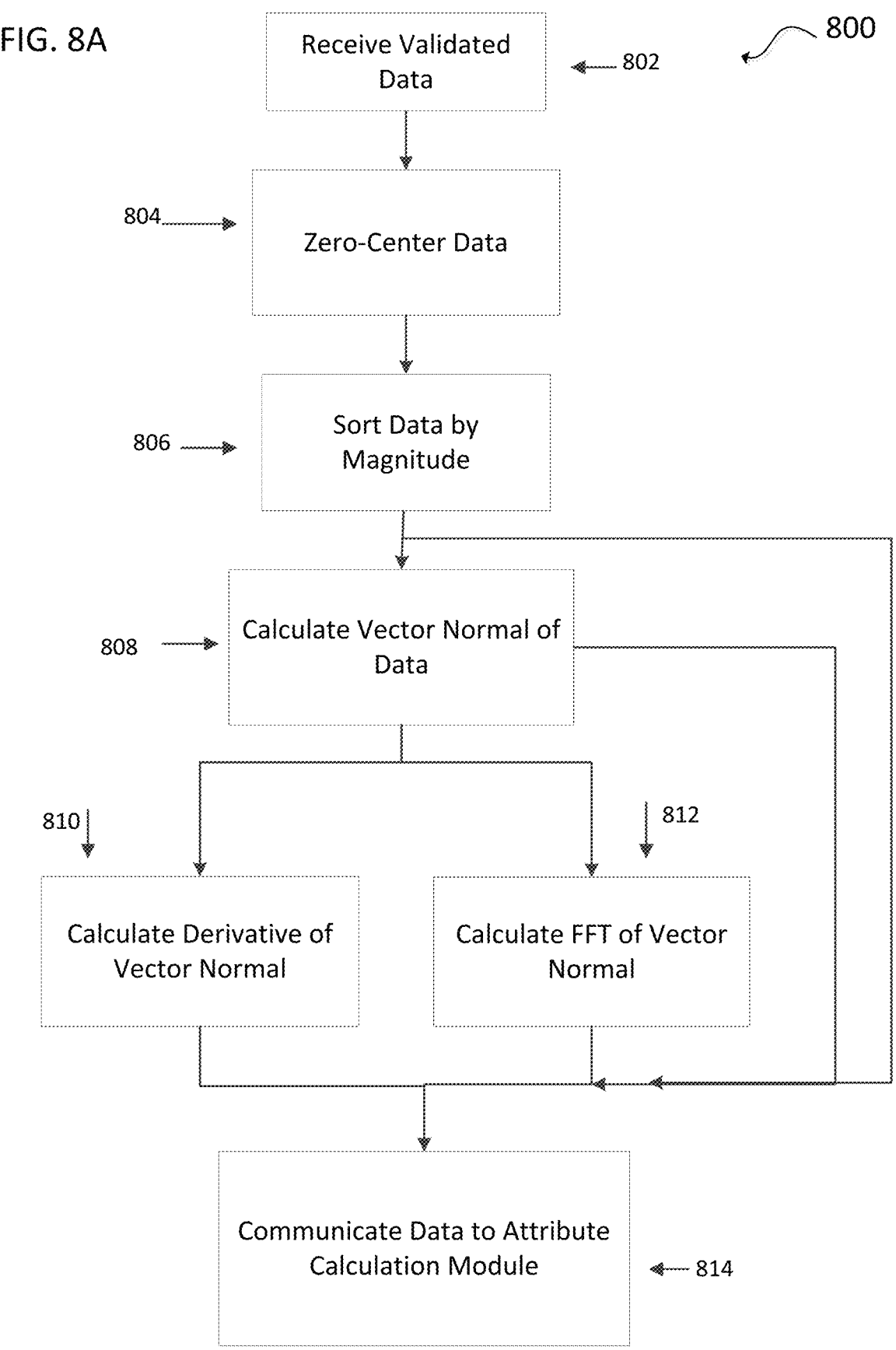

CALCULATING PACE AND ENERGY EXPENDITURE FROM ATHLETIC MOVEMENT ATTRIBUTES

CROSS-REFERENCE TO RELATED APPLICATIONS

This application claims priority to U.S. Patent Application No. 61/890,748, entitled "CALCULATING ENERGY EXPENDITURE FROM ATHLETIC MOVEMENTS," filed Oct. 14, 2013, and U.S. Provisional Patent Application No. 61/900,203, entitled "CALCULATING PACE AND ENERGY EXPENDITURE FROM ATHLETIC MOVEMENT ATTRIBUTES," filed on Nov. 5, 2013, which are expressly incorporated herein by reference in their entireties for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using athletic activity services and systems.

Many existing services and devices fail to provide accurate assessment of the user's energy expenditure, such as caloric burn, during physical activity. Therefore, users are unaware of the benefits that certain activities, which may include daily routines that are often not thought of as being a "workout", are to their health. Existing devices for allowing users to monitor their energy expenditure often suffer from one or more deficiencies, including: cumbersome collection systems, inaccurate measurements that are beyond an acceptable threshold, unacceptable latency in reporting the values, erroneous classification of activities based upon detected motions of the user, failure to account for deviations between different users, improperly including repetitive behavior as being classified as a specific activity, such as for example, running and/or walking, relatively high power consumption, and/or a combination of these or other deficiencies.

Therefore, improved systems and methods to address at least one or more of these shortcomings in the art are desired.

BRIEF SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects relate to systems and methods configured to process motion data associated with a user. Motion data may be utilized, such as for example transformed, to calculate motion attributes from the data. The sensor may be worn by the user in certain embodiments. In certain implementations, it may be worn on an appendage of the user. In further embodiments, at least one sensor is not in physical contact with the user.

One or more motion attributes from a dataset may be calculated without classifying the motion data into an activity type (such as walking, running, swimming, or any specific or general activity). One or more motion attributes may be compared to one or more activity models comprising motion data from a plurality of individuals. The plurality of individuals may not include the user. In certain embodiments, both the motion data within the models and the motion attributes of the user are independent of any activity type. Various models may be used to calculate different values. For example, in certain embodiments, the attributes may be compared to select an energy expenditure model from the one or more energy expenditure models, which may be selected as a best-match to the one or more motion attributes. The selected energy expenditure model may then be used to calculate an energy expenditure associated with the motion of the user.

In certain embodiments, the entire process is conducted on a single device, which may be worn by a user. Data points generated by the user's motion may be generated during a performance of a first activity type, but at least one of the activity models is devoid of motion data collected during any individual's performance of the first activity type. One or more motion attributes are calculated as either: (a) omni-directional attributes from sensor data that includes a value for each of an x-axis, a y-axis, and a z-axis, or (b) unidirectional attributes from sensor data that includes a value for one of an x-axis, a y-axis, or a z-axis. In other embodiments, the one or more motion attributes are calculated from one or more data points representing variation between the motion data point outputs from the sensor. In one embodiment, a first sensor may comprise an accelerometer and heart rate data may be obtained from the user during the user's performance of the motion detected by the sensor. In one such embodiment, it may be determined to cease utilizing heart rate data despite being accurate based upon the accelerometer providing data indicative that the user has reduced their physical activity below a threshold amount for at least a first time frame.

In certain embodiments using data from an accelerometer or other sensor with multiple axes may be used. Referring to an example with an accelerometer, motion data from a first axis having the greatest amount of acceleration for a first time period may be determined and a second axis having the second greatest amount of acceleration for the first time period may also be determined. Based upon the identification of the first accelerometer axis, a first attribute for the motion data along the first axis may be calculated and based upon the identification of the second accelerometer axis, a second attribute for the motion data along the second axis may be calculated. In certain embodiments, the second attribute is different than the first attribute. A cumulative attribute from cumulative motion data collected from at least the first and the second accelerometer axes may also be determined. The attributes may be compared to attributes of one or more activity models comprising motion data from a plurality of individuals, without regard to an activity type of the data to select an energy expenditure model from the one or more energy expenditure models. Using the selected energy expenditure model, an energy expenditure associated with the motion of the user may be calculated.

BRIEF DESCRIPTION OF THE DRAWINGS

FIGS. 8A-8B show flowchart diagrams that may be implemented to transform received sensor data in accordance with one embodiment;

FIG. 12A shows a graph plotting FFT power against frequency data that includes data within an arm swing range and data within the bounce range; and FIG. 12B shows the same graph with a threshold utilized to determine if peaks within the bounce range meet a criterion in accordance with one implementation;

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
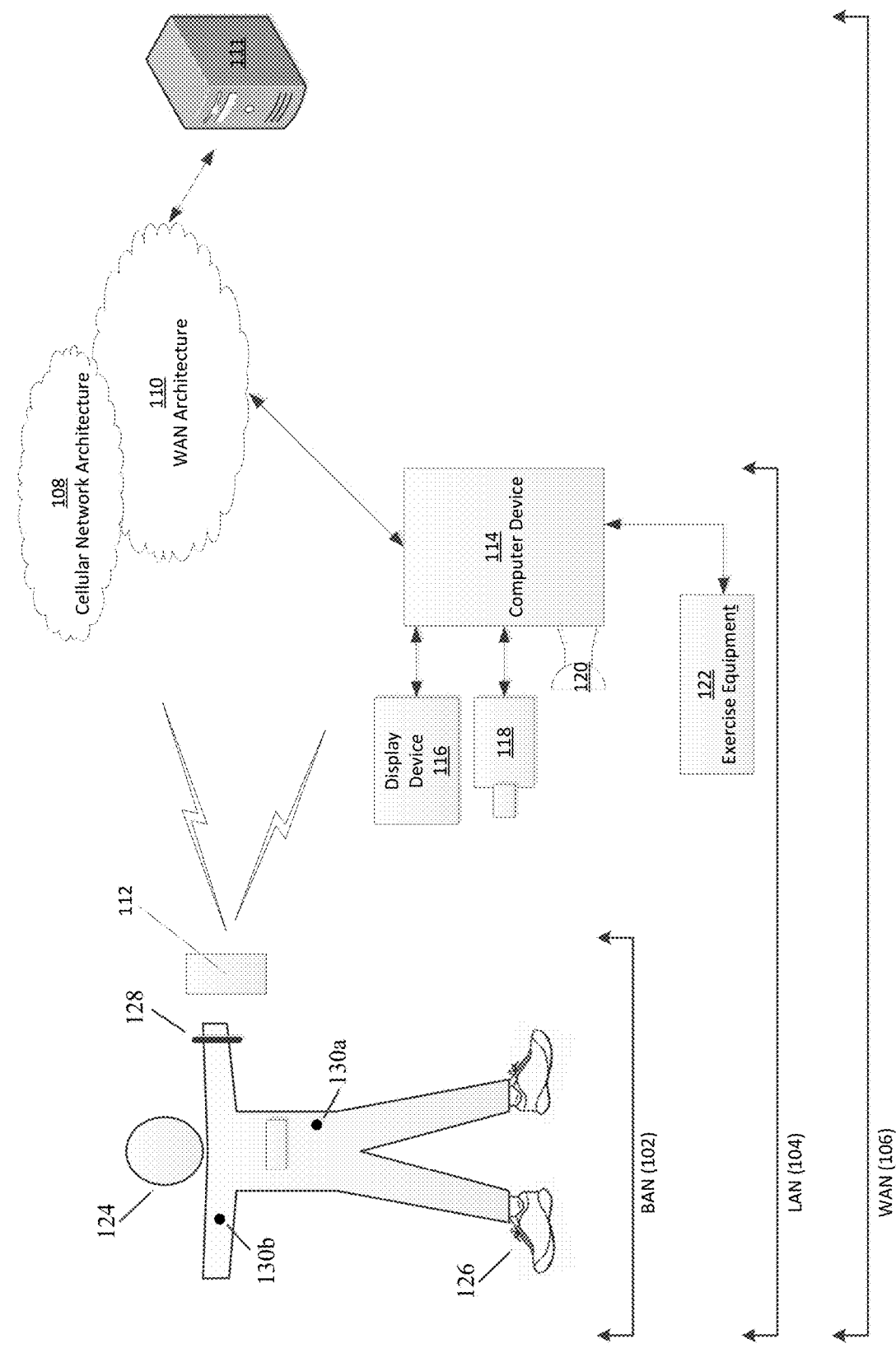
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
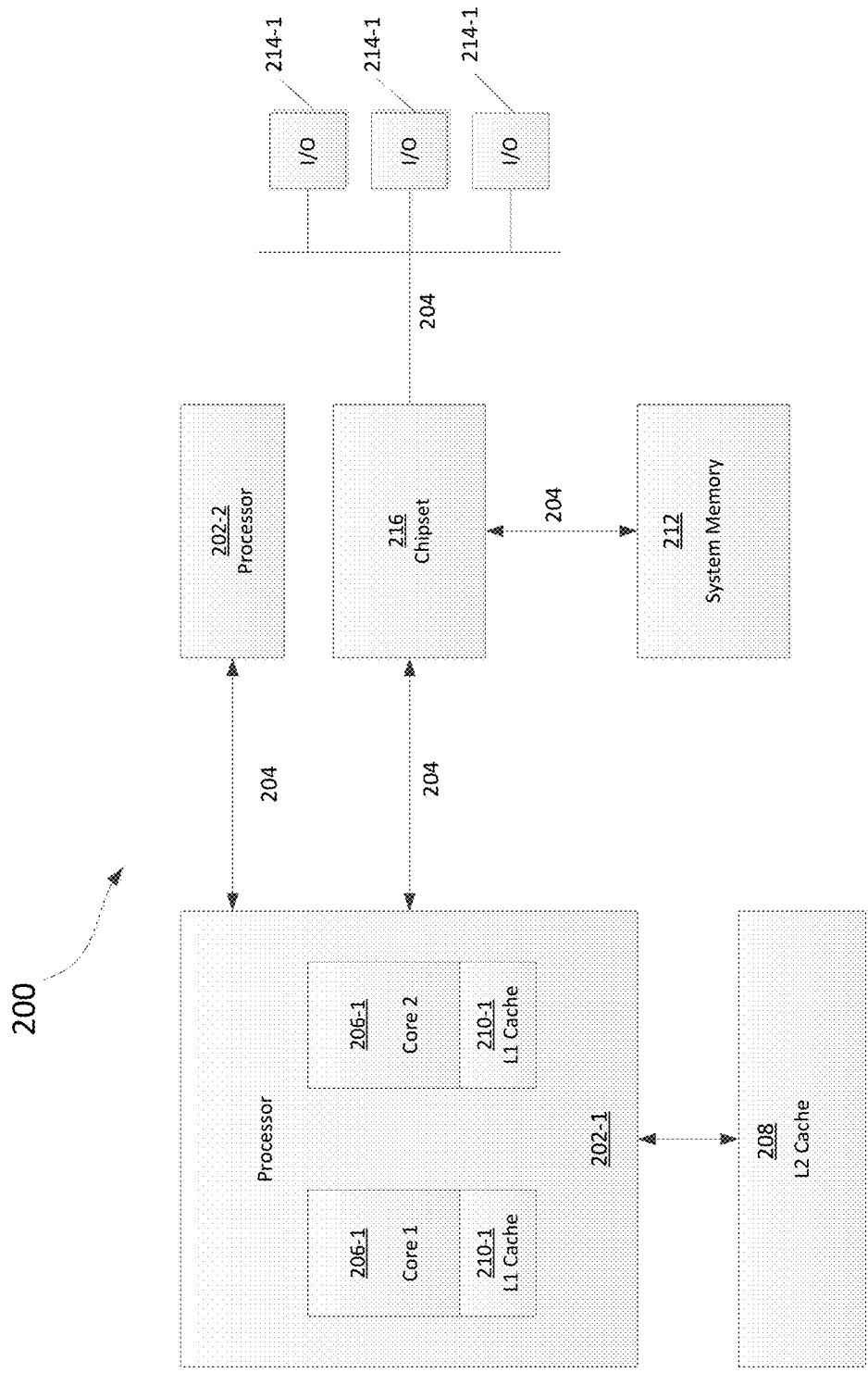
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
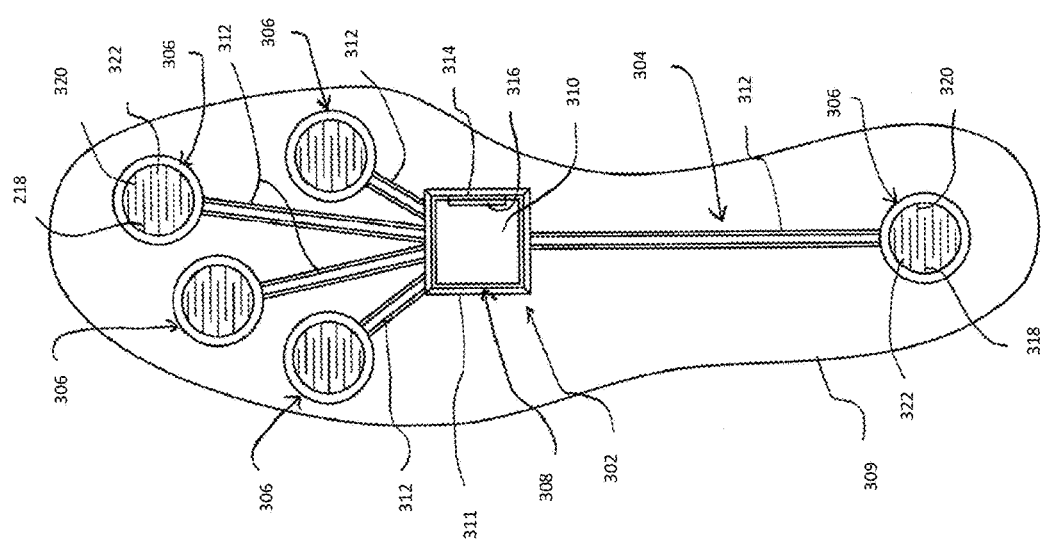
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
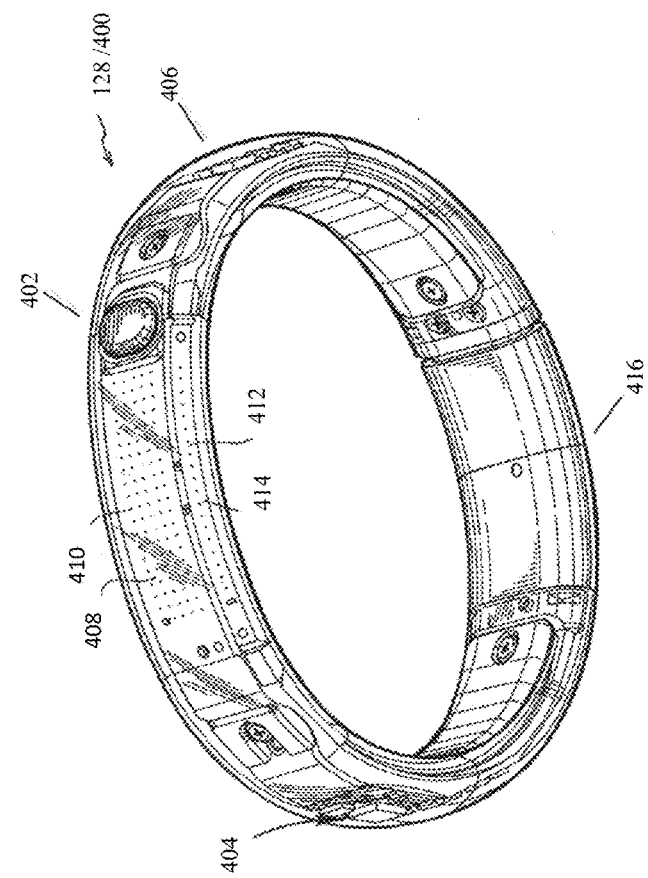
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130*a* and 130*b* may be sensors integrated into apparel, such as athletic clothing. Such sensors may be placed at any desired location of the body of user 124. Sensors 130*a/b* may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
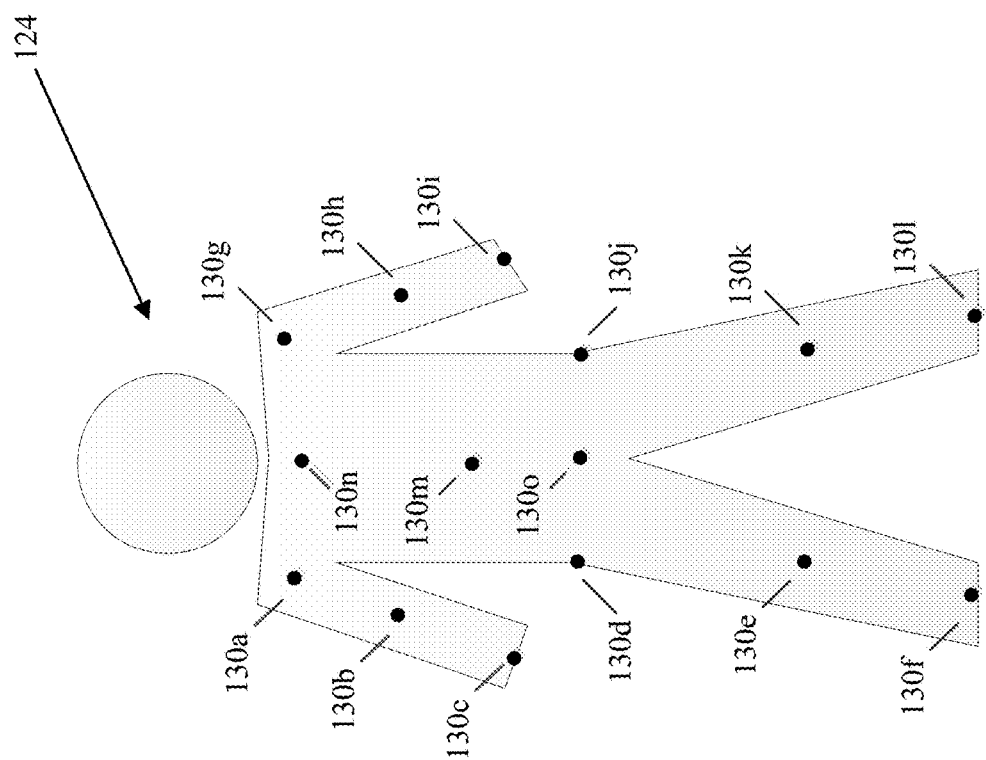
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Example Metrics Calculations

Aspects of this disclosure relate to systems and methods that may be utilized to calculate one or more activity metrics of an athlete, including but not limited to energy expenditure, speed, distance, pace, power, and/or others. The calculations may be performed in real time, such that the user may obtain real-time feedback during one or more activities. In certain embodiments, all calculations for a plurality of metrics are be estimated using a same set of attributes, or a sub-set of attributes from a common group of attributes, and the like. In one embodiment, a calculation of energy expenditure may be performed on a first set of attributes and without classifying the activity being performed by the athlete, such as being walking, running, playing a specific sport, or conducting a specific activity. In one embodiment, determinations of energy expenditure are done without any activity type templates, such that as the energy expenditure may be calculated from sensor data and/or derivatives thereof, without classifying the activity type. For example, energy expenditure may be calculated in accordance with certain embodiments using the same set of attributes regardless of whether the athlete is performing a first activity or a second activity, such as for example, walking or playing soccer.

In certain implementations, calculations of energy expenditure calculated may be performed using a first set of attributes and another metric, such as for example, speed may be determined from the same set of attributes or a subset of the same attributes. In one embodiment, determination of a plurality of metrics may be conducted using a selection of core attributes. In one example, this attribute calculation may be used to estimate energy expenditure and/or a speed of walking and/or running of the user. In one example, an energy expenditure and/or speed of walking and/or running may be estimated using a same set of attributes, or a sub-set of attributes from a common group of attributes, and the like.

The systems and methods described herein may compare calculated attributes from activity data (real-time activity data, and the like) to one or more models wherein the one or more models may not include data captured for the activity type that the athlete performed (and may not be categorized, such as for energy expenditure calculations). In this way, the one or more models may be agnostic to the specific activity being performed by a user. For example, an activity device may receive information from a user performing a basketball activity and at least one model may not contain any data from basketball activities.

As an example of calculating multiple metrics, systems and methods may be implemented to determine whether to calculate speed for one or more time windows of data. Certain aspects of this disclosure relate to determinations of speed or distance that comprises categorizing athletic data. As discussed above, however, other aspects relate to calculating energy expenditure values without categorizing the athletic data into activity types (walking, running, basketball, sprinting, soccer, football, etc.), however, categorizing at least a portion of the same data utilized to calculate energy expenditure for the calculation of other metrics, such as for example, speed and/or distance is within the scope of this disclosure. In one implementation, speed (or another metric) may be determined from at least a portion of data derived from the determination of energy expenditure values. In accordance with certain embodiments, the attributes are calculated on a single device, such as any device disclosed herein or known in the art. In one embodiment, the attributes and calculation of the metrics are calculated on a single device. In one such example, a device configured to be worn on an appendage of a user may be configured to receive sensor data and calculate the attributes and a plurality of metrics from the attributes. In one embodiment, the single device comprises at least one sensor configured capture data utilized to calculate at least one attribute. In accordance with certain embodiments, the attributes are calculated from one or more sensors located on the single device.

Example Energy Expenditure Calculations

Figure 6:
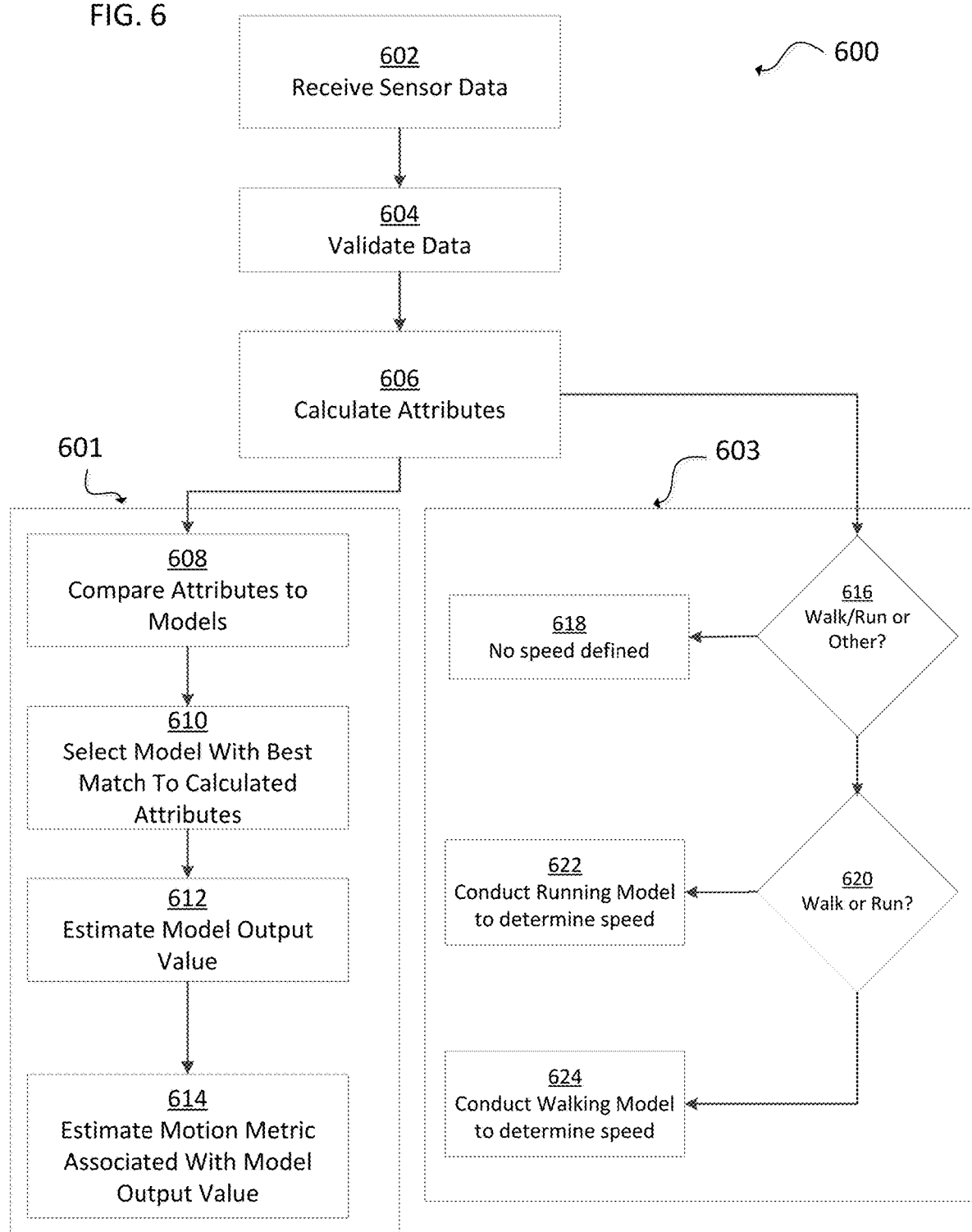
FIG. 6 shows an example flowchart that may be implemented to metrics, including energy expenditure and speed.

One or more of the systems and methods described herein may calculate an estimate of energy expenditure that implements at least one of the components of FIG. 6. In one configuration, a device, such as device 112, 126, 128, 130, and/or 400 may capture data associated with one or more activities being performed by a user, and may include one or more sensors, including, but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. This captured activity data may, in turn, be used to calculate one or more energy expenditure values associated with the user.

In one implementation, an estimation of the volume of oxygen consumed by a person may be used in the calculation of an effective metabolic equivalent or an estimation of energy expenditure by said person. For example, in one embodiment, a liter of oxygen consumed by a person may be associated with an energy expenditure of approximately 5 kilocalories (5 kcal). Additionally or alternatively, those of ordinary skill in the art will recognize various alternative methodologies exist for utilizing in calculations of energy expenditure based upon oxygen consumption by a person.

In one embodiment, oxygen consumption by a person may be measured as a volume of oxygen per unit mass, such as per kilogram ($VO_2$/kg). In one implementation, the systems and methods described herein may utilize values, such as stored as computer-executable instructions on one or more non-transitory computer-readable mediums related to actual and/or estimated oxygen consumption associated with specific activities. In certain embodiments, the values may be actual data or derived from actual data collected from one or more individuals performing one or more specific activities, and otherwise referred to as training data. For example, the systems and methods described herein may utilize training data related to oxygen consumption by one or more individuals performing activities including, among others, playing basketball, playing soccer, playing tennis, walking, jogging, running, and sprinting, sitting, squatting, and/or combinations thereof. Those of ordinary skill in the art will recognize various testing procedures that may be utilized to monitor oxygen consumption while an individual is performing one or more prescribed activities. Additionally, it will be readily understood to those of ordinary skill in the art that multiple oxygen consumption data points may be collected during an activity. Furthermore, one or more data manipulation processes may be performed on said collected data points to calculate, among others, an average oxygen consumption during a specific activity, and based on a recorded mass (e.g., measured in kilograms, and the like), and/or individual or class specific information (e.g., sex, weigh, height, age, percent body fat, among others).

In one implementation, training data may be recorded for one or more individuals performing one or more specific activities, wherein said training data includes information related to a volume of oxygen consumed at one or more time points during the one or more specific activities, and information related to individual and or class-specific information (e.g., the mass of the individuals performing the specific activities). Additionally, training data may include sensor data from a device, such as device 112, 126, 128, 130, and/or 400. In this way, the training day that may store information related to one or more sensor outputs in addition to information related to one or more volumes of oxygen consumed during one or more activities. In one implementation the sensor data stored in addition to the oxygen consumption data may include data from one or more of an accelerometer, a gyroscope, a location-determining device (e.g., GPS), light sensor, temperature sensor (including ambient temperature and/or body temperature), heart rate monitor, image-capturing sensor, moisture sensor and/or combinations thereof. For example, training data may include stored data from an accelerometer sensor, in addition to information related to a volume of oxygen consumed during an activity, for example, playing soccer.

Accordingly, the systems and methods described herein may include training data that includes one or more calculated attributes associated with an activity. Furthermore, the one or more attributes associated with an activity may include one or more volumes of oxygen consumed per unit mass of a person at one or more time points during an activity, and/or one or more calculated values based on one or more outputs from sensors associated with a device monitoring one or more motions of a user during said activity. For example, in one implementation, an output of an accelerometer sensor may include an acceleration value for each of the three axes (x-, y-, and z-axis). Accordingly, in one implementation, a plurality of acceleration values associated with the respective axes to which an accelerometer sensor is sensitive (x-, y-, and z-axis) may be grouped as a single acceleration data point. In another implementation, acceleration values may be processed by a processor, such as processor 202, associated with a device, such as device 112, 126, 128, 130, and/or 400 to calculate one or more attributes.

In one example, one or more data points received from a sensor aggregated into a dataset representative of one or more motions of user. Accordingly, the one or more data points may be processed to represent the data in a way that allows for one or more trends and/or metrics to be extracted from the data. In one example, acceleration data output from an accelerometer may be processed (transformed) to calculate a vector normal ("vector norm"). Additional or alternative transformations may be employed to calculate, in one example, a standard deviation of the vector normal, a derivative of the vector normal, and/or a Fast Fourier Transform (FFT) of the vector normal. Those skilled in the art will appreciate that certain transformations may combine sensor data from two or more sensors and/or with other data, such as biographical data (e.g., height, age, weight, etc.). In other embodiments, transformation may only utilize data from single sensors, such that sensor data from multiple sensors is not mixed. Transformations related to received motion data points are explained in further detail in relation to FIGS. 8A and 8B.

In one example, one or more attributes may be calculated from the received data, and wherein the attributes may be calculated subsequent to one or more transformation processes be executed on a dataset representative of one or more motions of a user. In this regard, datasets from multiple users may be used as a comparison against a user whose activity is not within the dataset. This may be done without categorizing the user's activity into an activity type (e.g., walking, running, playing specific sport) and in certain embodiments, the user may be performing an activity that was not conducted as part of collecting the training data within the data used to obtain attribute values for the models. Examples of attribute calculations are explained in further detail in relation to FIGS. 9A-9E.

In another example, the systems and methods described herein may be implemented to estimate one or more metrics from sensor data. These metrics may include, among others, an estimation of energy expenditure, an estimation as to whether a user is running, walking, or performing other activity, and/or an estimation of a speed and a distance (a pace) which a user is moving, and the like. For example, block 601 of flowchart 600 from FIG. 6 shows an example implementation of calculating energy expenditure from one or more attributes. Separately, block 603 is directed to an example implementation for calculating speed, which may be determined using one or more calculated attributes, which may be derived from the same sensors, from the same data, and/or the same attributes as the energy expenditure metric.

Accordingly, the systems and methods described herein may utilize data received from one or more different sensor types, including, among others, an accelerometer, a heart rate sensor, a gyroscope, a location-determining device (e.g., GPS), light (including non-visible light) sensor, temperature sensor (including ambient temperature and/or body temperature), sleep pattern sensors, image-capturing sensor, moisture sensor, force sensor, compass, angular rate sensor, and/or combinations thereof.

Furthermore, while the example of attributes associated with acceleration data output from an accelerometer sensor are described, those of ordinary skill will appreciate that other sensors may be used, alone or in combination with other sensors and devices, without departing from the scope of this disclosure. For example, a heart rate monitor may be used, wherein the data output from a heart rate monitor may output data representative of a heart rate in units of beats per minute (BPM) or equivalent. Accordingly, one or more transformations may be performed on outputted heart rate data to interpolate a heart rate signal between heart rate data points, and allowing for signal dropouts at certain points. Furthermore, the attributes calculated for sensor data associated with a heart rate monitor, or any other sensor, may be the same, or may be different to those described above in relation to accelerometer data.

In another implementation, the systems and methods described herein may analyze sensor data from combinations of sensors. For example, a device may receive information related to a heart rate of a user from a heart rate monitor, in addition to information related to motion of one or more appendages of a user (from one or more accelerometers, and the like). In one example, the device may determine that a user has a heart rate indicative of vigorous exercise, but accelerometer data may indicate that said user has been at rest for a period of time. Accordingly the device may determine that the user has a sustained elevated heart rate after a period of activity but is now resting after said activity, and the like.

In one implementation, training data may be used to construct one or more models, otherwise referred to as experts, or expert models, for predicting, among others, a volume of oxygen consumption based upon (at least in part) one or more individual-specific properties such as a gender, a mass and/or a height of a user. Accordingly, information from one or more sensors associated with a device, such as device 112, 126, 128, 130, and/or 400, may be used to calculate one or more attributes. In turn, the calculated attributes may be compared to attributes associated with one or more constructed models, and thereby, used to predict a volume of oxygen being consumed by a user while outputting motion signals (sensor output values) corresponding to the calculated attributes. For example, a user may be performing an activity, such as playing soccer, while wearing a sensor device on an appendage. The sensor device, in turn, may output sensor values, which may be processed to calculate one or more attributes. Subsequently, the one or more calculated attributes may be compared to one or more attributes associated with one or more models, and an estimation of a volume of oxygen being consumed by the user while playing soccer may be made. Furthermore, said estimation of a volume of oxygen being consumed may be used to estimate energy expenditure values by the user playing soccer. This process is described in further detail in relation to FIG. 6. In certain embodiments, all of the sensor data comes from a unitary device. In one example, the unitary device is an appendage-worn device. In certain configurations, the appendage worn device comprises at least one of an accelerometer, a location-determining sensor (e.g., GPS) and a heart rate monitor. In another example, the unitary device comprises a sensor configured to be placed on or within athletic apparel, such as a shoe. In yet another example, a sensor from at least two different devices are utilized to collect the data. In at least one embodiment, the device comprising a sensor utilized to capture data is also configured to provide an output of energy expenditure. In one embodiment, the device comprises a display device configured to display an output relating to energy expenditure. In further embodiments, the device may comprise a communication element configured to transmit information relating to energy expenditure to a remote device.

In another implementation, one or more attributes may be calculated from received sensor data and used as inputs to one or more walking and/or running models for predicting, among others, a speed/a pace of a user. Further details of such an implementation are described in relation to block 603 of flowchart 600.

FIG. 6 is a flowchart showing an exemplary implementation of attribute calculation. In one example, this attribute calculation may be used to estimate one or more metrics associated with an activity being performed by a user, and wherein said estimation may include an energy expenditure speed, and/or one or more other metrics. In one example, an energy expenditure and/or speed of walking and/or running may be estimated using a same set of attributes, or a sub-set of attributes from a common group of attributes, and the like.

Information related to the movement of the user may be outputted as one or more data signals from one or more sensors associated with one or more sensor devices monitoring the user. In one implementation, FIG. 6 represents one or more processes carried out by at least one processor, such as processor unit 202, which may be associated with a sensor device, such as, among others, device 112, 126, 128, 130, and/or 400. Accordingly, devices may not directly monitor a volume of oxygen being consumed by a user during an activity. In one implementation, one or more sensor devices may monitor one or more motions associated with one or more activities being performed by a user. Furthermore, in one arrangement, received activity data may be correlated with observed oxygen consumption values for activities that may exhibit certain attributes, and associated with one or more oxygen consumption models.

One or more embodiments receive sensor data from one or more sensors (see, e.g., block 602). In certain embodiments, the sensor data may be associated with a device worn by a user. In one example, and as previously described, said device may be, among others, device 112, 126, 128, 130, and/or 400. Accordingly, the sensor data may be received by a processor, such as processor 202 from FIG. 2, and may be received from one or more sensors described herein and/or known in the art. In one implementation, sensor data may be received at block 602 from an accelerometer at a frequency of, among others, 25 Hz. Additionally or alternatively, sensor data may be received from the sensor, such as accelerometer, in windows of between 5.0 and 5.5 seconds. In one embodiment, the window (or time frame) may be about 5.12 seconds in length. A window may be a period of time during which sensor data is recorded for one or more motions of a user associated with one or more activities being performed by a user. In one implementation, a sample window may include 128 samples (data points) of sensor data, wherein a sample of sensor data may include a value for each of three orthogonal axes of an accelerometer (x-axis, y-axis, and z-axis), and/or a vector normal value. In yet another implementation, sensor data received from, in one implementation, an accelerometer, may be received in windows that do not overlap (e.g., 5.12 second-length groups of sensor data each containing 128 samples, and received singly, rather than simultaneously, and/or discrete from each other). However, in alternative embodiments, those of ordinary skill will readily understand that the systems and methods described herein may be employed with any frequency of operation of an accelerometer, with a window length measuring any length of time, and using any number of samples of sensor data from within a given window. Data may be validated as it is received, such as for, for example, at block 604. Data validation may include, among others, a person of one or more values of received sensor data to one or more threshold values, and the like. Various examples of example data validation embodiments are described in further detail in relation to FIG. 7.

Further aspects of this disclosure relate to calculating one or more attributes from the data (see, e.g., block 606). Calculation of one or more attributes may occur after validation protocols, such as those described herein, including in relation to FIG. 7. In one implementation, one or more attributes may be calculated for one or more of the received samples in a sample window (e.g., the 128 sample window described above). Attribute calculation may occur in real-time as the data is collected. Various example embodiments that may be implemented to calculate one or more attributes are described in greater detail in relation to FIGS. 9A-9E.

Further embodiments may compare one or more calculated attributes associated with data received from one or more sensors, and indicative of one or more activities being performed by a user, to one or more attributes associated with one or more models. In one example, one or more attributes may be compared to one or more models (see e.g., block 608). For example, for calculations of energy expenditure, one or more attributes may be compared to oxygen consumption models. In another example, attributes may be used as inputs to one or more of, among others, models for estimation of a number of steps (during walking), strides (during running), or other movements by a user, and/or models for estimation of speed and distance (pace) of a user (see e.g., block 603 of flowchart 600, FIG. 15A-15C, and/or FIG. 16). Furthermore, as will be apparent from FIG. 6, one or more calculated attributes may be used as inputs to one or more models such that, in one example, a model for estimation of an energy expenditure may be executed separately from a model for calculation of a step rate, a walking speed, and/or a running speed, and the like. As previously described, one or more models may be stored in a memory, such as memory 212, and the like, and associated with a device, including a sensor device.

In one implementation, a model may include information (e.g. training data) collected during one or more user's performance conducting one or more activities and, in one example, predicted oxygen consumption. The models may include training data from activities that, despite being different from the activity that an athlete is performing, may have similar relationships between attributes. As such, the models may serve as accurate predictors of oxygen consumption. Accordingly, a model may include training data associated with one or more different activities. For example, a model may include training data received from one or monitoring processes associated with, among others, playing soccer and playing basketball. In this way, oxygen consumption data associated with certain movements of soccer and basketball activity data may be similar (within one or more predetermined numerical ranges for different periods during the activities, and the like).

In another implementation, a first oxygen consumption model may comprise data from a same one or more users as those one or more users' data used in a second oxygen consumption model. In another configuration, a first model and a second model may use a same one or more users' data. In yet another configuration, a data associated with a model may have been captured from a same one or more users during a single data collection period, or from multiple collection periods across a same or a different day, and the like. In one implementation, a first model may be associated with data from a first group of one or more sensors and a second model may be associated with a second group of one or more sensors, and wherein the first group may share one or more, or none of the same sensor types. In one implementation, the systems and methods described herein may compare calculated attributes from activity data (real-time activity data, and the like) to one or more models wherein the one or more models may not include data captured for that activity type. In this way the one or more models may be agnostic to the specific activity being performed by a user. For example, an activity device may receive information from a user performing a basketball activity. In response, the device may process the received basketball activity data (such as, for example, block 606 of flowchart 600), and compare calculated attributes to one or more models (such as, for example, block 608). In one implementation, the one or more models may or may not comprise data related to basketball. In this way, the computed one or more attributes for received sensor data may correspond to one or more models, and wherein the models need not comprise training data related to the specific activity being performed by a user.

In one configuration, a plurality of models, each with their own attributes, which may or may not overlap attributes of other models, may be utilized. In one example implementation, each model may be associated with 20 attributes. In another configuration, the systems and methods described herein may store 5, 10, 15 or 21 attributes for each model. However it will be readily understood to those of ordinary skill that the systems and methods described herein may store any number of attributes in association with each model, and in certain embodiments a first number of attributes stored in association with a first model may differ from a second number of attributes stored in association with a second model. Furthermore, the one or more attributes stored in association with a model may be alternatively referred to as weights, or may be used to calculate related weighting values that may be used to compare a model to those attributes calculated from sensor data received from a device. Accordingly, in one implementation, the number of attributes calculated from data received from a sensor device (or multiple sensor devices) collecting movement data of a user may be equal to a number of attributes, or alternatively, a number of weights associated with one or more stored oxygen consumption models.

One or more aspects may calculate a probability that a first model will provide the most accurate estimation of oxygen consumption from the total number of stored one or more models. For example, a probability that a specific model, from a group of different (e.g., 16) models is most likely to provide the most accurate output of oxygen consumption may be calculated. The calculations may be performed, for example, as part of block 608, and be based on one or more attributes calculated from received sensor data indicative of an activity being performed by a user. In one implementation, a level of closeness between attributes calculated from received sensor data, and those attributes, or alternatively, those weights, associated with one or more of the stored oxygen consumption models may be calculated, such as for example as part of block 608. In one implementation, the systems and methods described herein may execute one or more processes to compare input attributes with corresponding weights associated with a stored model (expert). In one example, block 608 may calculate a probability for each stored model. Accordingly, said probability may represent a likelihood that the calculated one or more attributes are a best-fit for a given model. For example, a probability may be calculated for each of 16 stored models, and the like. The highest probability value, from the 16 calculated probabilities, indicates the model with the best-fit for the calculated attributes, and the like. Further details related to a comparison of calculated attributes to stored models, and subsequent selection of a best-fit model for those calculated attributes, are explained in relation to FIG. 14.

In one example, block 610 represents one or more processes to select a model with a best-match, or best-fit to those calculated attributes from block 608. As previously described, said best-fit model represents stored training data that most closely approximates the data received from a sensor device monitoring an activity of the user. In one implementation, the best-fit model may be the model corresponding to a calculated probability value that is closest to a value of 1.0. In another implementation, block 610 may select two or more models. For example, models fitting within a predefined deviation, variation, and/or threshold may be selected (referred to as a hybrid-model strategy).

As shown by illustrative block 612, one or more embodiments may estimate an output value from a selected model (expert). In one example, an output may be in estimation of a volume of oxygen consumption as a result of one or more activities being performed by a user. Accordingly, in one example, block 612 may correlate an activity being performed by a user with an estimated oxygen consumption value, and based on a selected model (e.g., a best-fit model) that most closely matches attribute values calculated from sensor data. In one implementation, a model may store one or more estimates of oxygen consumption, wherein the one or more estimates of oxygen consumption may be stored based on at least one individual-specific value, such as a gender, a weight and/or a height of a user. Accordingly, and based upon the one or more attributes associated with the sensor data received from a sensor device, block 612 may return an estimate of a volume of oxygen consumption by the user based upon an activity carried out by the user.

Block 614 may be implemented to estimate a motion metric associated with a model output value. In one example, a motion metric may be an energy expenditure value, which may be estimated using an oxygen consumption value. As previously described, one or more methods may be utilized to calculate an energy expenditure from an oxygen consumption value. In one example, an estimated energy expenditure of 5 kcal is associated with an oxygen consumption of 1 L by a user. However those of ordinary skill in the art will recognize various other formulae for calculating energy expenditure based upon a value of oxygen consumption, and using one or more individual-specific values (e.g., a height and a weight of a user).

In another implementation, one or more attributes calculated (including, e.g., at block 606) may be used in a determination of whether sensor data is indicative of walking, running, or another activity being performed by a user, and additionally or alternatively, the speed at which the user is walking or running, and the like. Accordingly, one or more attributes calculated at block 606 may be used as inputs to block 603. In particular, one or more attributes may be communicated from block 606 to decision block 616. At block 616, one or more processes may be executed to determine whether a user is running or walking, or performing another activity. Further details related to these one or more processes are described in relation to FIGS. 15A-15C. If it is determined that a user is performing an activity other than running or walking, flowchart proceeds from block 616 to 618. Accordingly, for a user performing activity other than running or walking, no processes are executed to define the speed at which the user is traveling, and the like. If it is determined, at decision 616, that's the user is running or walking, decision 620 may be implemented to determine whether the activity is walking or running Example embodiments for selecting an activity, such as running or walking, are provided herein, including in relation to In one embodiment, if it is determined that a user is running, one or more attributes may be communicated to a running model, such as to determine speed (e.g., see block 622). If, however, it is determined that a user is walking, certain embodiments may communicate one or more attributes to a walking model, such as to determined speed (e.g., block 624).

Figure 7:
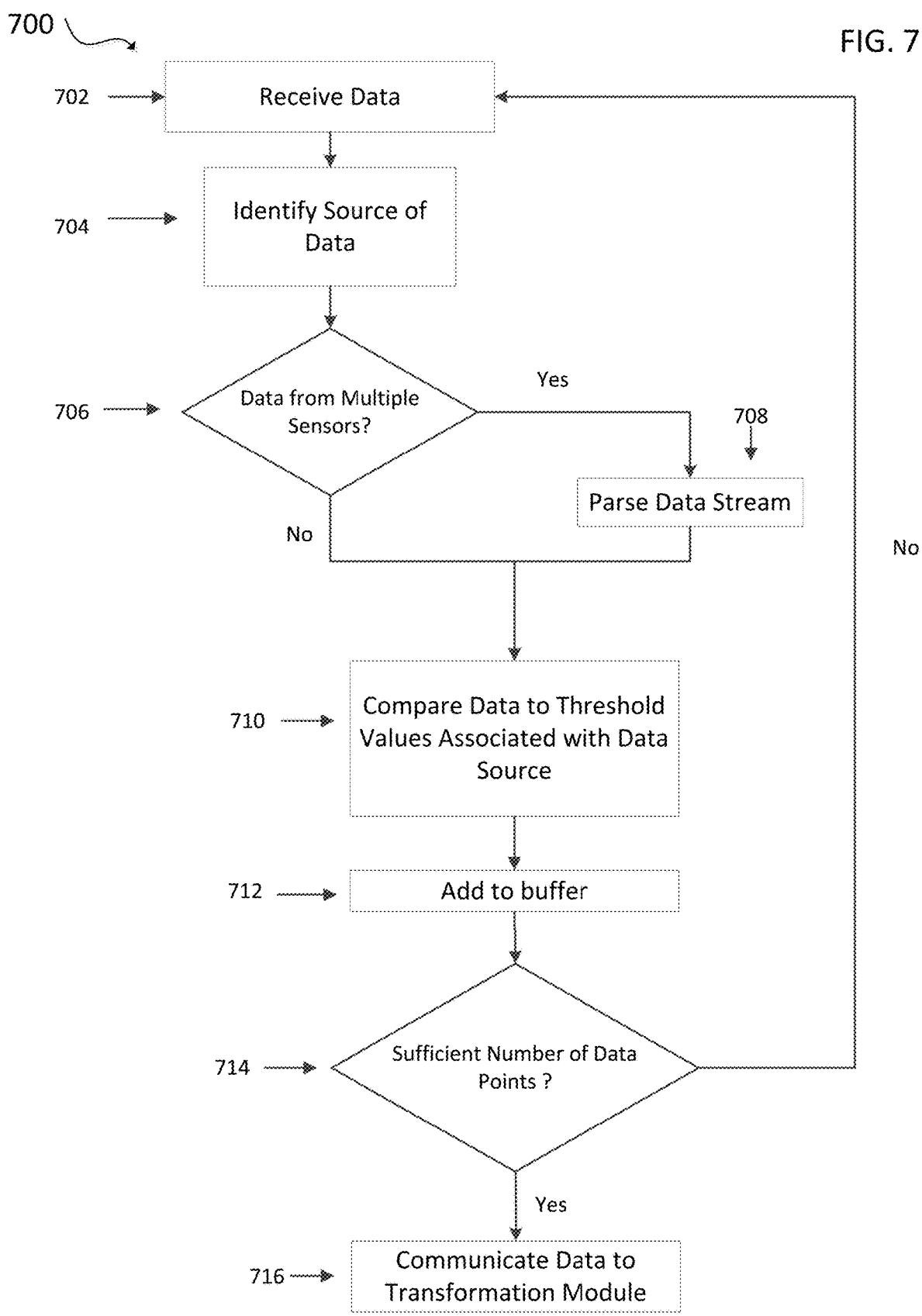
FIG. 7 shows a flowchart that may be implemented to validate received sensor data in accordance with one embodiment.

FIG. 7 depicts a flowchart 700 showing an example implementation that may be utilized in the verification of data received from one or more sensors. In one example, flowchart 700, either in whole or in part, may be implemented as part of executing verification implementations of block 604 from FIG. 6. Block 702 may represent one or more processes for receiving data from one or more sensors. As previously described, data may be received from sensors of different types, including, but not limited to, accelerometers, heart rate monitors, gyroscopes, location-determining device (e.g., GPS), light (including non-visible light) sensor, temperature sensor (including ambient temperature and/or body temperature), sleep pattern sensors, image-capturing sensor, moisture sensor, force sensor, compass, angular rate sensor, and/or combinations thereof. Data may be received, at block 702, as one or more data points, or samples. Furthermore, data may be received as part of a continuous, or in intermittent data stream. Additionally, and as will be readily understood to those of ordinary skill in the art, data received at block 702 may be from a single sensor, or multiple sensors, and may be received as a serial input, or as a parallel import (simultaneously). Block 702 may encompass portions of block 602 in certain embodiments.

Block 704 may include one or more processes to identify a source of received data. Accordingly, block 704 may identify a sensor type from which data is received. In one implementation, the information contained within a data point (a sample) may include an identification of a sensor type, sub-type, model and/or specific instance of a sensor from which the data was generated and communicated. For example, block 704 may identify received data that has been received from an accelerometer, and the like. In another example, block 706 of flowchart 700 may identify the received data as being from one or more sensors. If one or more received data points are received from separate sensors, f the data stream may be parsed (e.g., block 708). In one example, block 708 may be implemented to separate received data points based upon a sensor type from which the data has been received, and the like.

A value of a received data point may be compared to one or more threshold values (e.g., 710). Accordingly, block 710 may validate a received data point. In this way, a data point may be identified as representing a motion of a user, and distinguished from one or more values representing noise, and the like. For example, for an accelerometer data point, a threshold value may be, among others, 10% of a maximum output value from an accelerometer sensor. Accordingly, if a received data point from an accelerometer has a numerical value (in one example, an absolute numerical value, and the like), of less than 10% of the maximum output value from the accelerometer sensor, the data point may be identified as noise, and disregarded. Correspondingly, if the received data point from an accelerometer has a numerical value of greater than 10% of the maximum output value from the accelerometer sensor, the data point is it identified as a valid acceleration.

Those of ordinary skill in the art will recognize that a threshold value may take any numerical value, or otherwise, that is appropriate for a particular sensor type, and based upon, among others, an output range of numerical values from a particular sensor type. Furthermore, the exemplary 10% threshold associated with an accelerometer may additionally or alternatively be a 5% threshold, a 15% threshold, a 20% threshold, or 25% threshold, or any other numerical value, and the like. Furthermore, there may be more than one threshold associated with a specific sensor type. For example, a sensor may have two or more thresholds associated with data outputs. A first threshold may distinguish between noise and true acceleration data, and may be, for example, a 10% threshold. Furthermore, a second threshold may distinguish between true acceleration data and saturated data, and may be, for example, a 95% threshold, and the like.

Data from multiple sensors or inputs may be validated, such as at block 710. As one example, one or more data points from a heart rate sensor, wherein a heart rate sensor data point may be compared to one or more thresholds. In one example, if a received heart rate is between 20 and 220 bpm, the heart rate data point is considered proper, and maybe subsequently communicated to a data buffer, such that the buffer described in relation to block 712, and the like. In another example, a validation of heart rate sensor data may execute one or more processes to check that a number of heart rate data points are within a one or more predetermined beats per minute thresholds while a buffer is being populated with acceleration data.

One or more data points may be validated as being representative of useful data, such as for example at block 710, wherein useful data may be representative of one or more activities or performances being carried out by a user. Accordingly, subsequent to validation of one or more data points, the validated data points may be stored (temporarily or otherwise) in a buffer (see, e.g., block 712). Those of ordinary skill in the art will understand that's various types of buffers may be used without departing from the scope of this disclosure. Accordingly, in one example, a buffer may be a dedicated hardware chip that includes elements configured for storage of digital information. A buffer may be implemented in a form of persistent memory, such as a hard disk drive (HDD), a solid state drive (SDD), an optical disk, and the like. Additionally or alternatively, buffer may be implemented in a form of volatile memory, such as, among others random access memory (RAM), and the like.

Certain embodiments may be configured to add one or more data points to a buffer, wherein said buffer may, in one example, store 128 data points (samples) before communicating the contents of the buffer to a transformation module. Those of ordinary skill in the art will recognize that, in one example, fewer than 128 data points may be stored in the buffer. For example, the buffer may store 64 samples, 32 samples, 16 samples, and the like. Similarly, those of ordinary skill will recognize that, in another example, greater than 128 data points may be stored in the buffer, and without departing from the scope of the disclosure described herein. Additionally or alternatively, the number of samples and/or data points stored in a buffer may be dependent upon the sensor type from which the data is received. For example, data received from an accelerometer may occupy more storage space than data received from a heart rate monitor, and the like. Furthermore, in one example, a transformation module may include one or more processes for manipulating and/or identifying features of received data, and the like.

In one implementation, a time stamp may be associated with a data point as it is added to the buffer. In another implementation, a timestamp may be associated with a validated data point independently of a buffer, and the like.

Certain embodiments may confirm whether a threshold number of data points are within a buffer, or series of buffers (see, e.g., block 714). In this way, block 714 may represent one or more processes to identify the number of stored data points and a buffer, and compare this stored number of data points to a threshold number of data points before flowchart 700 proceeds to block 716. For example, block 714 may check the number of data points stored in a buffer, and compare this number of stored data points to a threshold number of 128 data points, and the like. In one example, once block 714 identifies 128 samples stored in a buffer, flowchart 700 proceeds to block 716, wherein the 128 samples are communicated to a data transformation module. If, however, block 714 determines that the number of samples stored in a buffer is less than a threshold number of, for example, 128 samples, flowchart 700 proceeds to block 702 for processing of additional data points, and the like. Those of ordinary skill will recognize that block 714 may be omitted from flowchart 700, without departing from the scope of the disclosure, and one or more data points may be communicated to a transformation module continuously, and without having received a threshold number of data points, and the like.

In accordance with one embodiment, a threshold of 128 data points may represent a window of data, wherein a window of data, which if collected at a frequency of 25 Hz would result in a length of time of about 5.12 seconds. Accordingly, a sample window may comprise a number of samples other than 128, sampled at any given frequency, and for any length of time, and the like. Furthermore, a transformation module may be one or more processes configured to execute on data received from one or more sensors. The one or more transformation processes may aggregate data into a dataset, wherein a dataset may be a group of data points representative of a motion and/or an activity of a user, and the like. Accordingly, data transformation processes are described in further detail in relation to FIGS. 8A and 8B.

FIG. 8A is a flowchart diagram 800 that includes one or more exemplary processes for transforming received sensor data. In one example, validated data, which may be validated in accordance with one or more teachings set forth in FIG. 7, may be received (e.g., block 802). In one configuration, flowchart 800 may represent one or more processes to transform data received from an accelerometer sensor. Accordingly, a data point output from an accelerometer may include a data value associated with one or more of three orthogonal axes (x-axis, y-axis, z-axis), and the like. In one specific implementation, an accelerometer may output a numerical value representative of an acceleration along a single axis (a single axis selected from one or more of an x-axis, y-axis, or z-axis), and on a scale of 0 to 1024. Those of ordinary skill in the art will recognize that accelerometers manufactured by different companies, or indeed, sensors of different types, will output numerical values different to those described herein. In this specific example, an output value of 1 to 512 may represent an acceleration in a negative direction along an axis. Correspondingly, an output value of 513 to 1024 may represent an acceleration in a positive direction along said same axis. Block 804 of flowchart 800 may execute one or more processes to zero-center one or more data points output from an accelerometer, and the like. Zero-centering data, in one implementation, may be used to transform data values associated with one or more data points on accelerometer such that acceleration of 0 m/s$^2$, is outputted with numerical value of zero, and the like. In one example, one or more processes to zero-centered data may include subtracting 512 from an output value from an accelerometer. As such, an acceleration along a negative direction of an axis may be represented by a negative value from −1 to −512, and an acceleration along a positive direction of an axis may be represented by a positive value of +1 to +512, and the like.

In one example, data points associated with an accelerometer may include one or more numerical values representing one or more axes to which the accelerometer is sensitive to acceleration. For example, an accelerometer may output three numerical values associated with each of three orthogonal axes (x-axis, y-axis, and z-axis). In one example, the physical orientation of an accelerometer circuit and/or chip in a device, such as device 112, 126, 128, 130, and/or 400, may control the output values from the accelerometer. For example, an accelerometer positioned within a device in a first orientation may output acceleration values primarily along an x-axis during a first activity. However, the same accelerometer positioned within a device in a second orientation may output acceleration values primarily along a y-axis during said same first activity, and the like. As such, one or more processes may be dependent upon a physical orientation of accelerometer sensor within the device, and wherein the orientation of the sum accelerometer sensor may differ between two devices. In one implementation, however, block 806 may execute one or more processes to source data output from an accelerometer sensor based on a magnitude of the output values, and the like. For example, for each data point received from an accelerometer, one or more processes may execute to identify the axis, from a group of, in one implementation, three axes (x-axis, y-axis, and z-axis) with the highest value of acceleration. In one implementation the highest value of acceleration may be an absolute value, and the like. Accordingly, the axis corresponding to the highest value of acceleration may be re-labeled/re-ordered as the x-axis. Furthermore, the axis corresponding to the second highest value of acceleration may be re-labeled/re-ordered as the y-axis. Additionally, the axis corresponding to the third-highest value of acceleration may be re-labeled/re-ordered as the z-axis, and the like. In this way, re-ordering the axes by magnitude allows one or more subsequent data manipulation processes to be agnostic to the physical orientation of an accelerometer sensor within a device, such as device 112, 126, 128, 130, and/or 400, and the like.

In one example, block 808 may transform one or more data points received from an accelerometer sensor by calculating a vector normal of the received data. Those of ordinary skill in the art will recognize one or more processes to calculate a vector normal of a data point comprising three values representative of each of three orthogonal axes to which an accelerometer is sensitive. In one example, a vector normal may be calculated as a square roots of a sum of squares according to equation 1 below:

$$\text{Vector normal}=\text{SQRT}((x\_i)^2+(y\_i)^2+(z\_i)^2). \quad \text{(Equation 1)}$$

Given equation 1 above, those of ordinary skill in the art will recognize that x_i is a value of acceleration along an x-axis, y_i is a value of acceleration along a y-axis, and z_i is a value of acceleration along a z-axis, and the like.

Further transformations may be carried out on data received from a sensor, wherein said data may be received from an accelerometer sensor, and may be validated prior to transformation. In one example, block 810 represents a transformation to calculate a derivative of a vector normal. Accordingly, those of ordinary skill in the art will recognize various systems and methods for calculating a derivative, such as a derivative of a vector normal, and the like. In another example, block 812 represents a transformation to calculate a Fast Fourier Transform (FFT) of a vector normal. Similarly, those of ordinary skill in the art will recognize various systems and methods for calculating a FFT of data to represents a data in a frequency domain: the like.

Block 814 of flowchart 800 represents one or more processes to communicate transform data to an attribute calculation module. The transformed data may be represented as one or more of zero-centered data sorted by magnitude, vector normal data, derivative of vector normal data, and/or a FFT representation of vector normal data, among others. Additionally, an attribute calculation module may comprise one or more processes for extracting information from a dataset, wherein said the extracted information may characterize one or more motions and/or activities being performed by a user. In one example said extracted information may be referred to as one or more attributes of the data, and the like.

Figure 8B:
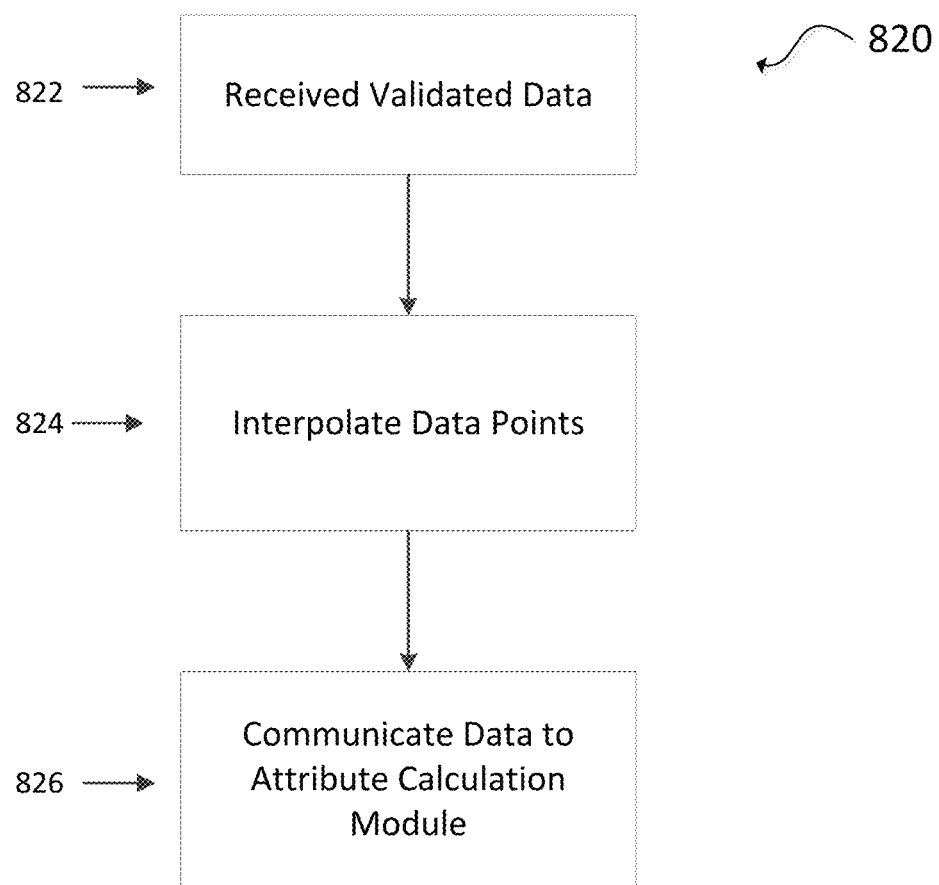

FIG. 8B depicts a flowchart 820, wherein flowchart 820 may comprise one or more processes for transforming received data, and the like. Block 822 of flowchart 820, in one example, may represent received of validated data. Data may be validated in accordance with one or more teachings herein, including the teachings in relation to, for example, to FIG. 7. In one example, the received validated data may be representative of one or more hearts rate data points received from a heart rate monitor, and the like.

In one example, block 824 may represent one or more processes to interpolate between received heart rate data points. For example, the rate at which data points representative of a heart rate of a user are received may be, among others, 1 Hz. In one implementation, it may be desirable to receive at least one or more than one heart rate data point per unit time (such as per second). Accordingly, in one implementation, interpolation between received heart rate data points may be employed to generate data points corresponding to a rate higher than 1 Hz, and the like. Subsequently, and as represented by block 826, one or more processes may be executed to communicate interpolated heart rate data points to an attribute calculation module, and the like.

Figure 9A:
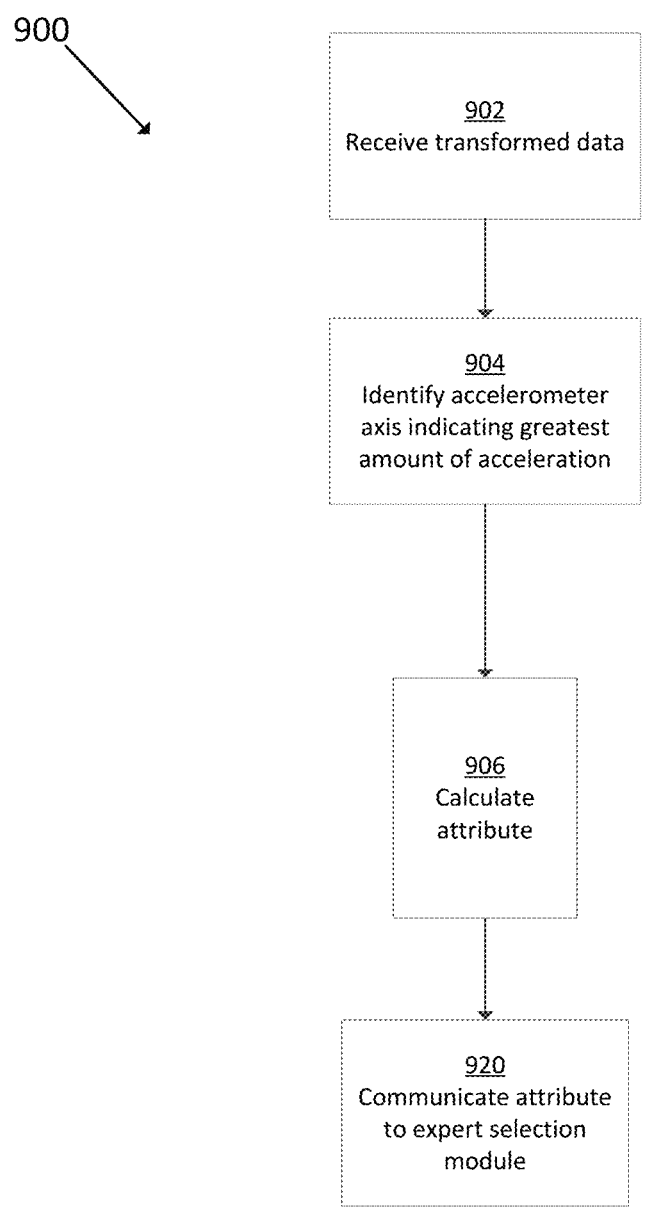
FIGS. 9A-9E show flowchart diagrams that may be implemented to calculate attributes from transformed sensor data in accordance with one embodiment.

FIG. 9A depicts an exemplary flowchart 900 that may include one or more processes for calculation of one or more attributes from received sensor data. In one example, data received from one or more sensors may be validated, and transformed prior to receipt by block 902. In another example, however, one or more data points may be communicated directly to block 902 without validation or transformation, and the like.

In one example, FIG. 9A may represent one or more processes to calculate one or more attributes from one or more received accelerometer data points. For example, block 904 of flowchart 900 may execute one or more processes to identify an accelerometer axis indicating a greatest amount of acceleration. In one example, and as a result of one or more sorting processes executed at block 806 of flowchart 800, the axis corresponding to a greatest amount of acceleration will be an x-axis, and the like. Accordingly, block 904 may identify those data values associated with an x-axis. However, those of ordinary skill in the art will understand that the acceleration values associated with highest acceleration may be re-ordered using one or more alternative methods, and such that an axis representing a highest amend of acceleration may differ between data points, or may be re-ordered to be a y-axis or a z-axis, and the like.

As previously described, an attribute may generally be a calculated value representing one or more motions of a user, or parts thereof, and which may be used to subsequently predict an output from a model. Furthermore, a model may be used to, among others, predict oxygen consumption by a user during an activity, and the like. A plurality of different attributes may be calculated from a single data point received from a sensor, or a group of data points/group of samples, otherwise referred to as a dataset, and the like. In one example, a group of attributes used to estimates, among others oxygen consumption by a user may include, a vector normal oven acceleration data point, a derivative of vector normal of an acceleration data point, and/or a Fast Fourier Transform of vector normal of an acceleration data point, as described in relation to FIG. 8A.

In another example, further specific attributes may be calculated from data received from an accelerometer. For example, an attribute may be calculated as a value representing one or more motions of a user, and associated with an acceleration signal from an accelerometer axis indicating a greatest amount of acceleration. In one example, an attribute calculated at block 906 may include a statistical value related to a data point received from an axis indicating the greatest amount acceleration, such as a mean value, and the like.

Block 920 represents one or more processes to calculate one or more attributes to an expert selection module. Accordingly, an expert selection module may comprise one or more processes to compare one or more calculated attributes to one or more expert models, wherein an expert model may be used to predict/estimates an output associated with an activity being performed by a user. In one example, such an output may be a volume of oxygen consumption by a user, and the like.

Figure 9B:
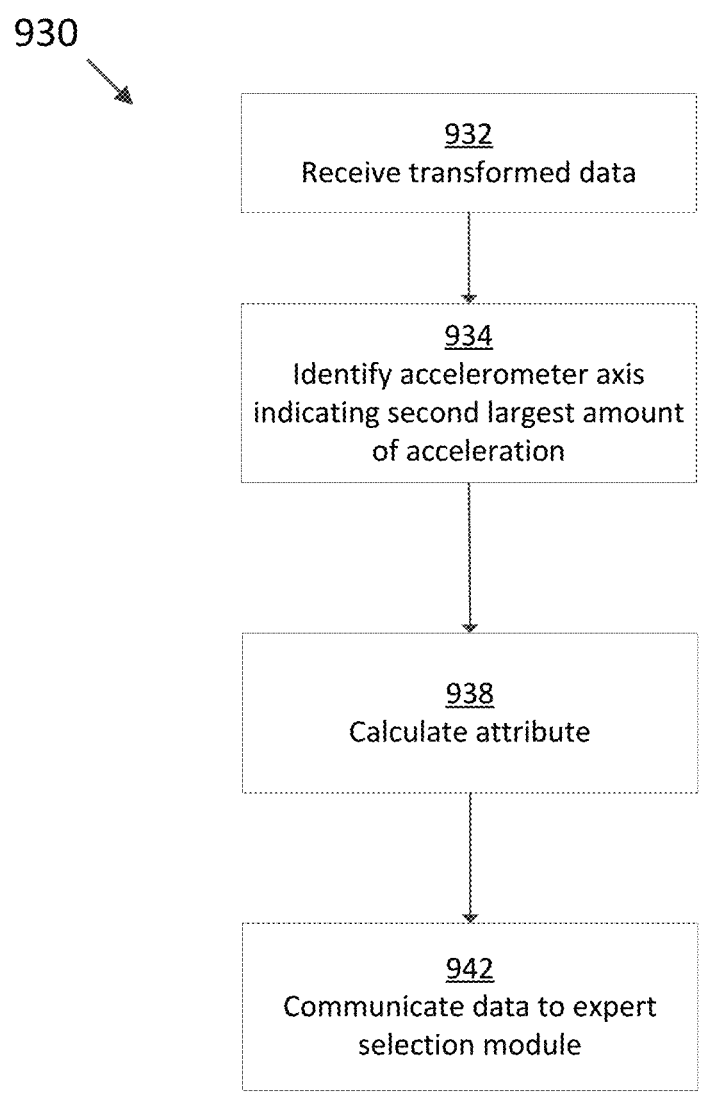

FIG. 9B includes a flowchart 930, wherein flowchart 930 may include one or more processes to calculate one or more attributes from received sensor data. Similar to FIG. 9A, block 932 of flowchart 930 represents one or more processes to receive transformed sensor data. Accordingly, data transformation is described in further detail in relation to FIG. 8A and FIG. 8B.

Block 934 of flowchart 930 may identify accelerometer axis indicating a second largest amount of acceleration. In one example, and subsequent to one or more transformation processes including one or more axis re-ordering processes, the axis indicating a second largest amount of acceleration may be a y-axis, and the like.

Block 938 may represent one or more processes to calculate an attribute from the received sensor data. In one example, a calculated attribute may be a statistical value. Furthermore, specific examples of attributes are described in relation to FIG. 17B, which may be similar to the processes that may be executed in relation to FIG. 9B, and the like. Subsequently, a calculated attribute may be communicated to an expert selection module, as described in relation to block 942.

Figure 9C:
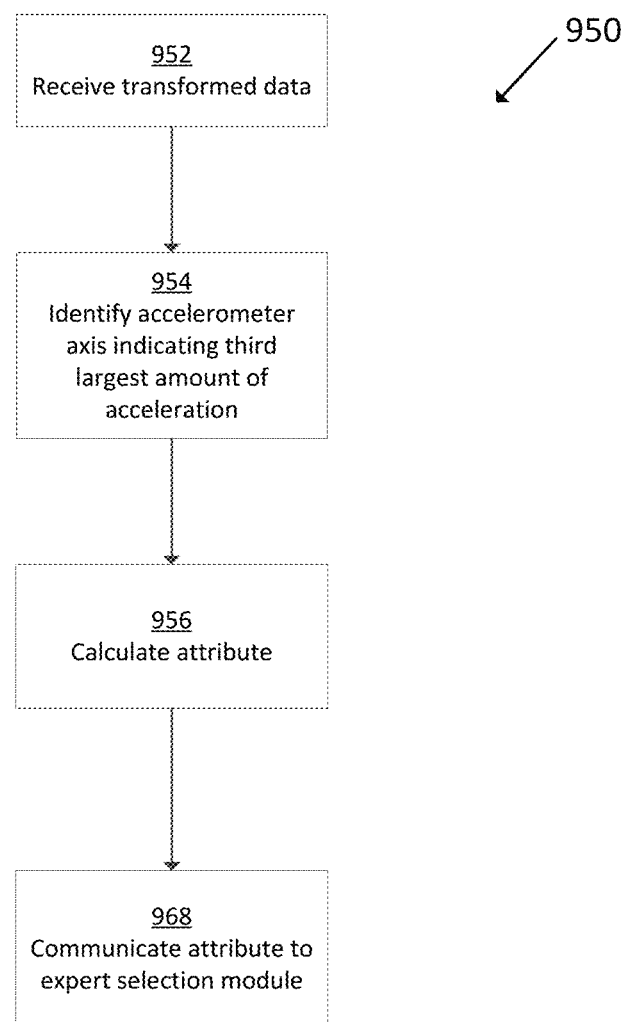

FIG. 9C depicts a flowchart 950 which may include one or more processes for calculating one or more attributes of received data, wherein the received data may be one or more data points from accelerometer, and the like. Accordingly, block 952 represents one or more processes to receive transformed data, wherein data transformations are described in relation to FIG. 8A and FIG. 8B. Alternatively, those of ordinary skill will recognize that the received data may not be transformed, such that received data at block 952 may, alternatively, be raw data received from one or more sensors.

Block 954 may represent one or more processes to identify data associated with an axis of accelerometer indicating a third largest amount of acceleration. In one example, and as described in relation to block 806 of FIG. 8A, the axis associated with a third largest amount of acceleration may be a z-axis.

Block 956 of flowchart 950 represents one or more processes to calculate an attribute from the received sensor data. In a similar manner to FIG. 9A and FIG. 9B, a calculated attribute may be a statistical value, such as a mean value of received data, and the like. Additional details related to population of one or more attributes are given in relation to FIG. 17C, which includes features similar to those described in relation to FIG. 9C.

Figure 14:
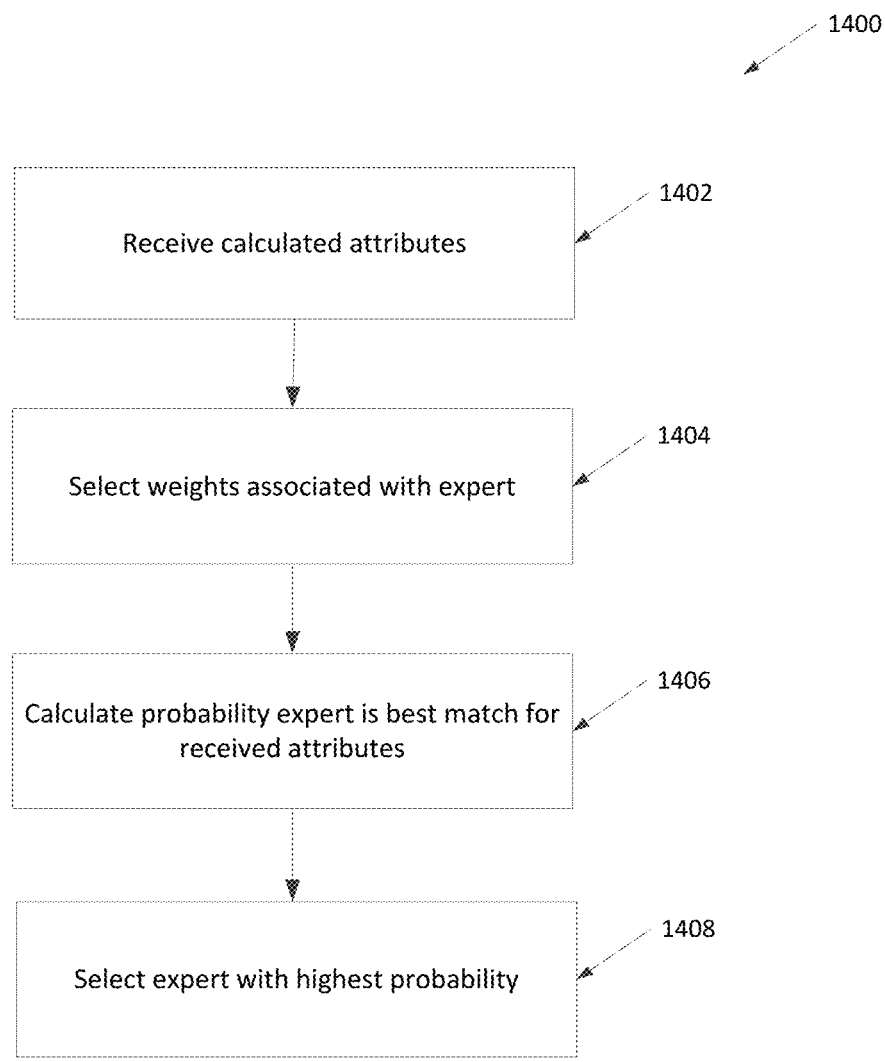
FIG. 14 shows a flowchart diagram that may be implemented to compare calculated attributes to expert models used to predict one or more output values associated with activities performed by a user.

Block 968 may execute one or more processes to communicate one or more calculated attributes to an expert selection module, wherein said expert selection module is described in relation to FIG. 14.

Figure 9D:
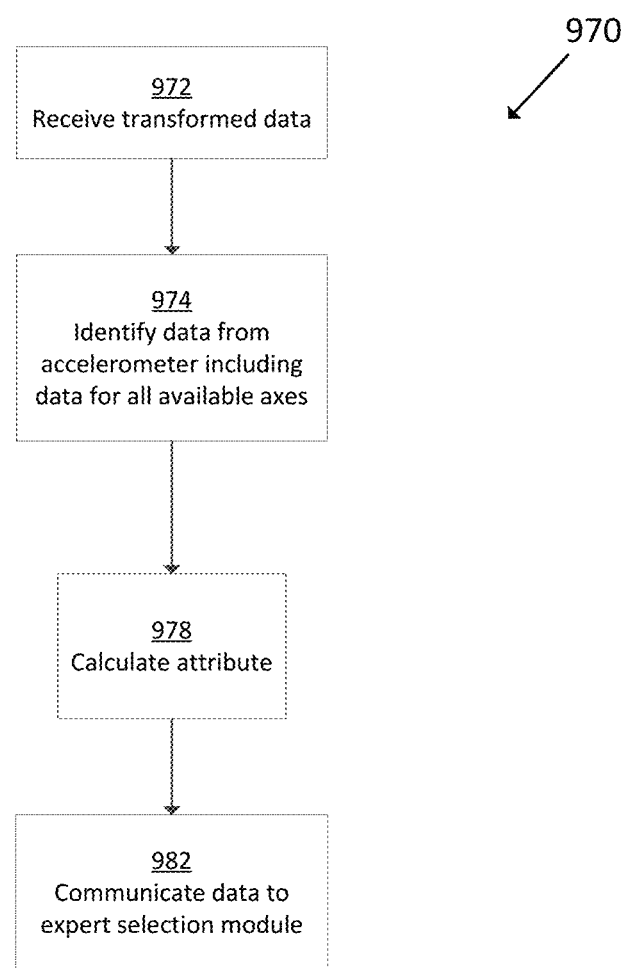

FIG. 9D is a flowchart diagram 970 which may represent one or more processes to calculate one or more attributes associated with received sensor data. For example, block 972 may receive transformed sensor data from accelerometer. Accordingly, block 974 may group those data points from all axes associated with the accelerometer. In one example, an accelerometer may output data related to one, two, or three orthogonal axes (x-axis, y-axis, and/or z-axis). Block 978 represents one or more processes to calculate an attribute from the received sensor data. As such, a calculated attribute may be a statistical value, such as a mean value of the received sensor data, and the like. Further details related to attribute calculation are given in relation to FIG. 17D, which includes elements similar to those described in relation to FIG. 9D.

Subsequent to calculation of one or more attributes, and as represented by block 982 of flowchart 970, one or more attributes may be communicated to an expert selection module. An expert selection module may be one or more processes associated with selecting a best-fit model associated with calculated attributes, and as described in further detail in relation to FIG. 14.

Figure 9E:
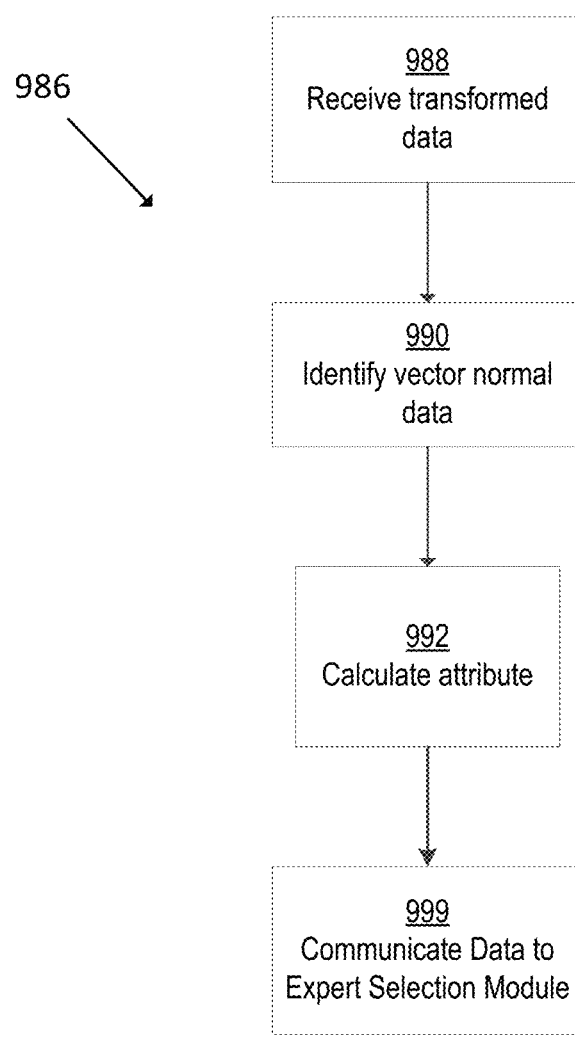

FIG. 9E is a flowchart diagram representing one or more processes to calculate attributes associated with received sensor data. In one example, flowchart 986 represents one or more attribute calculation processes associated with data received from an accelerometer, and the like. Accordingly, block 988 represents one or more processes to receive transformed accelerometer data. In one implementation, and as described in relation to FIG. 8A, accelerometer data may be transformed by calculation of a vector normal of said data, and the like. In one example, block 990 identifies a calculated vector normal of accelerometer data. From said calculated vector normal data, one or more attributes may be identified.

In one example, block 992 of flowchart 986 represents one or more processes to calculate an attribute from the received sensor data, and in particular, the vector normal data. In one example, a calculated attribute may be, among many others, a mean value of the vector normal data, and the like. Additional examples of attributes related to vector normal data are described in relation to FIG. 17E.

Subsequently, block 999 may communicate data to an expert selection module. An example expert selection module is described in further detail herein, including in relation FIG. 14.

Figure 10:
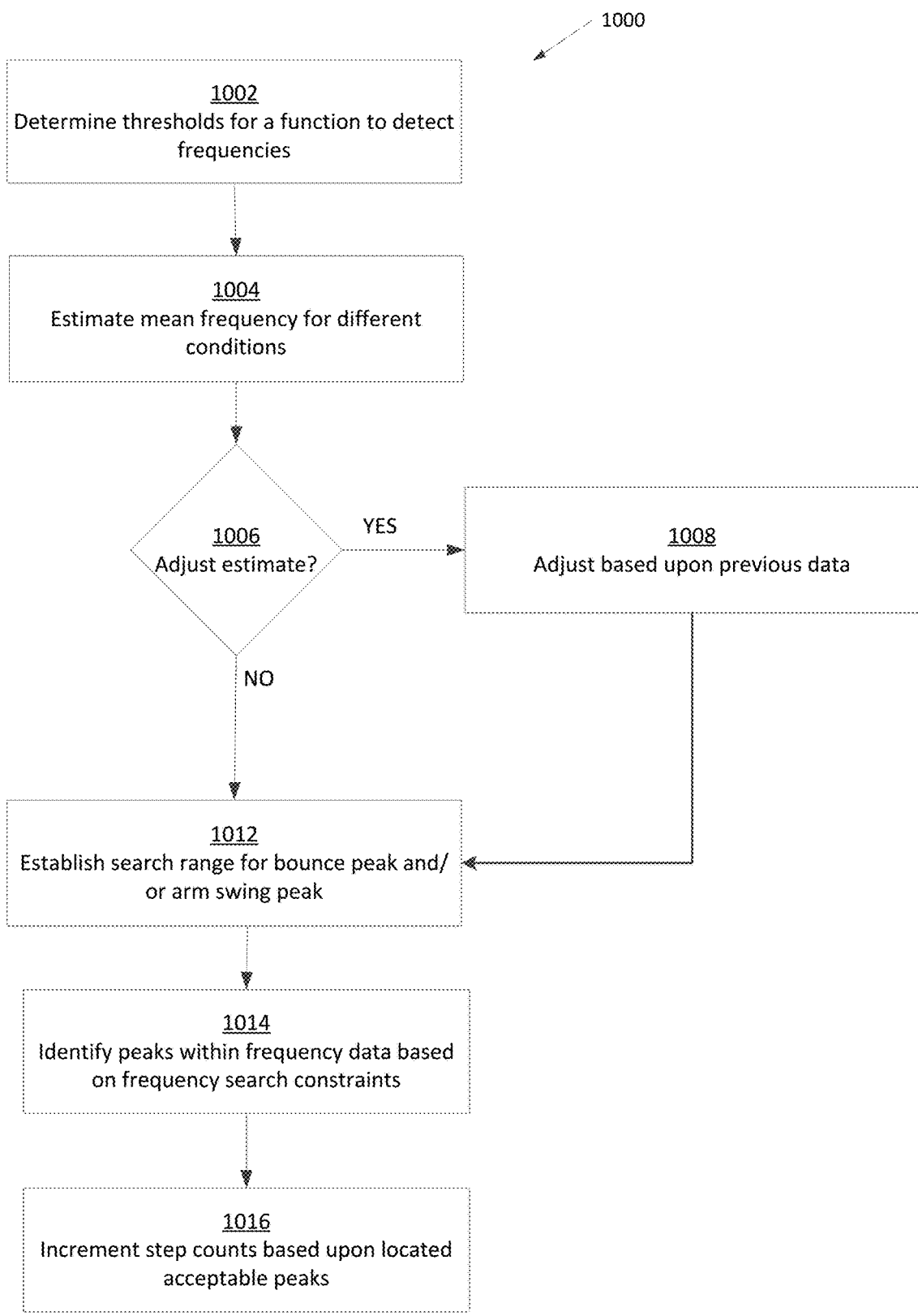
FIG. 10 shows an example flowchart that may estimate frequency and set up a frequency search range in accordance with one embodiment.

Although aspects of this disclosure relate to systems and methods configured to calculate energy expenditure without determinations whether a user is conducting an activity, such as running or walking, certain embodiments may determine step count, which may (either directly or indirectly) be used to calculate one or more attributes. In accordance with certain embodiments, systems and methods may be implemented to conduct frequency estimation and setting up frequency search ranges to locate peaks. In one embodiment, peak locating systems and methods may be utilized on data within a buffer, such as the analysis buffer. Yet in other embodiments, other data may be utilized, alone or in combination with data within the analysis buffer. FIG. 10 provides a flowchart 1000 showing one example process for estimating frequency. Those skilled in the art will appreciate that FIG. 10 is merely one of many embodiments that may be utilized in accordance with various implementations. One or more systems and methods may be implemented to identify a sub-group (or sub-groups) of peaks within the frequency data to utilize in the determinations of step quantification. In one embodiment, a FFT is performed and peaks in the FFT spectrum may be identified, such as with the thresholds and/or derivative around the peak. The performance of the FFT may occur before, during, or after initiating frequency estimation processes, such as one or more processes described in relation to FIG. 10. In further embodiments, the FFT may utilize one or more threshold and derivatives derived from one or more components of flowchart 1000.

In one embodiment, a specific peak (or peaks) within the data (such as for example, data obtained within a buffer and/or data obtained during a time frame) may be utilized. In one embodiment, "bounce peaks," "arm swing peaks," and/or other peaks may be identified. For example, many users "bounce" upon landing their feet when running. This bounce may provide frequency peaks within the data. Other peaks (and/or valleys) may be present within the sensor data. For example, many users often swing their arms in a predictable manner during running and/or walking to provide "arm swing peaks". For example, arms usually swing along an anterior/posterior axis (e.g., front to back). This frequency may be about half the frequency of the "bounce peaks". These peaks, however, may each vary independently, based upon, for example, the individual, the type of motion, the terrain, and/or a combination thereof.

In certain embodiments, thresholds for a function to detect frequencies may be determined or retrieved (e.g., block 1002). One or more systems or methods for determining identification criteria for locating peaks may estimate frequency of the data points. For example, an average (such as for example, a mean value) and/or a standard deviation (or variance) may be obtained. Such data may be utilized to determine "peaks" and "valleys" (e.g., the high and low values within the data), which may be quantified. Such data may be used in determinations of dynamic thresholds and/or derivative around the peak. In one embodiment, weighted averages, such as one or two-pass weighted moving averages of data in the buffer may be utilized in any determinations. In further embodiments, raw sensor data (e.g., accelerometer signals) may also be used, either alone or in combination with other attributes, such as derivatives of the data.

In one embodiment, a 1-pass weighted moving average, a 2-pass weighted average and raw data are each used. In another embodiment, only the 2-pass weighted moving average may be used. In one embodiment, the mean and standard deviation of the derivatives are calculated and may be used as threshold levels. In one embodiment, one or more processes may be utilized to obtain thresholds. For example, a first method may be utilized to locate peaks within a fixed range. Yet in certain embodiments, a second method may be utilized to determine identification criteria for locating peaks. In certain implementations, the first, second or additional methods may be implemented based, at least in part, on battery life. For example, the second method may require additional processing power, and therefore, may not be utilized upon receiving an indication that the battery life was decreased below a set point, and/or is declining at a rate above a threshold.

Figure 11:
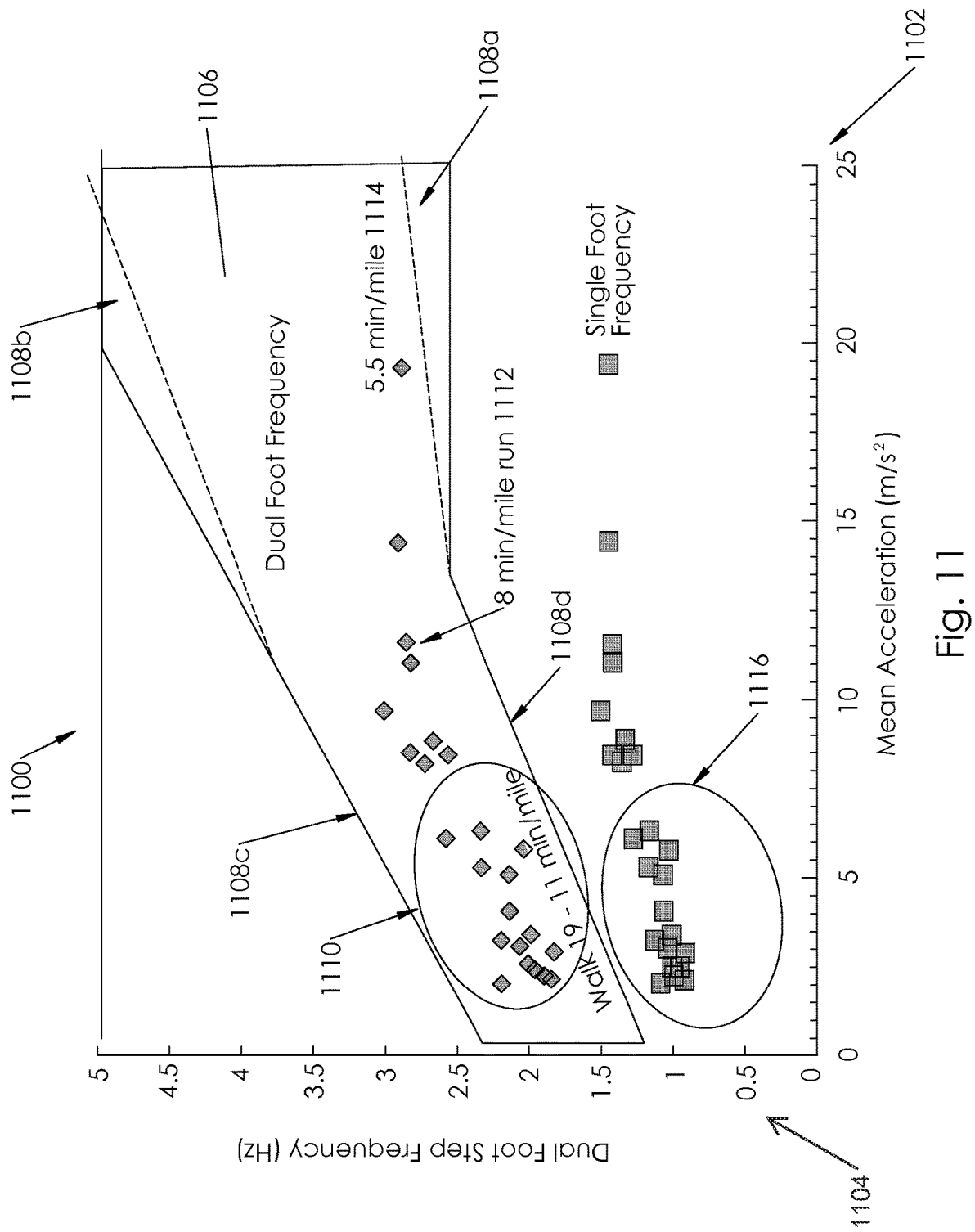
FIG. 11 shows a graph illustrating an example search range of motion data in accordance with certain embodiments.

At block 1004, a step frequency may be determined for the specific buffer (or groups of buffers). In certain embodiments, a mean acceleration of the buffer may be used to create a distinct narrow search range of the data (e.g., frequencies). For example, FIG. 11 shows graph 1100 showing the mean acceleration (expressed in meters per second squared "$m/s^2$") along x-axis 1102 and the frequency in Hertz (Hz) of the dual foot step frequency along y-axis 1104. Area 06 shows the detection area, which may be constrained by boundary lines 1108a-1108d. One or more of boundary lines 1108 may be based, at least in part, on the thresholds calculated at block 1002. Thus, if accelerations generate a frequency outside the frequency range that the accelerometry predicts (e.g., outside of boundary lines 1108a-1108d), then certain systems and methods may not utilize at least a portion of this data. This may be utilized to ensure data considered to be random noise (e.g. data with different frequency content but similar acceleration magnitudes). In one embodiment, a mean frequency may be approximated. In one embodiment, the mean frequency of sensor data measured along one or more axes may be calculated. For example, sensor data collected from one or more accelerometers may be used to determine the mean frequency along one or more of the x, y and z axes. For example, arm swing data may comprise components along each of the three axes, and thus measured. In one embodiment, the mean frequency for multiple axes may be approximated by examining the number of peaks and/or valleys in the data.

In accordance with certain embodiments, sensor data may be utilized to determine step count regardless of whether the step counts are responsive to walking and/or running. In this regard, it may be advantageous to retain sensor data comprising non-walking and/or non-walking data, rather determinations of walking and or running may be determined from attributes). For discussion purposes of example sensor readings, however, FIG. 11 is provided to show signals within the range of 0.5-2.4 Hz (located along y-axis 1104) which using other categorizing techniques may be considered as indicative of walking (see, e.g., samples designated by 1110). In another embodiment, signals within the range of 2.4 to 5 Hz may be considered as indicative of running in other categorizing techniques. For example, data points 1112 may indicate the athlete is running an 8-minute mile and data point 1114 may indicate that the athlete is running a 5.5 minute mile. Further, in certain embodiments, arm swing data may be utilized to determine the dual foot step frequency (see axis 1104). For example, if a wrist-worn device is configured to measure arm swings, such data may be interpreted as the single foot frequency. In this regard, single foot frequency data points designated by element 1116 may correspond to half the value (with respect to the y-axis 1104) to data points 1110. In one embodiment, therefore, the value of the single foot frequency may be doubled to arrive at the dual foot step frequency value. Those skilled in the art will appreciate that graph 1100 is no required to be generated or displayed, but rather is illustrated herein to demonstrate aspects of this disclosure.

Decision 1006 may be implemented to determine whether to adjust the estimated step frequency. In one embodiment, decision 1006 may consider whether steps were counted (or the frequency of steps) in a previous buffer, such as a preceding non-overlapping buffer. For example, decision 1006 may determine whether a successful FFT located steps in previous data. As would be appreciated in the art there may be situations in which the data (e.g., frequencies) change, however, the user may still be conducting the same activity, albeit at a different rate or pace. For example, if a user is running at 10 mph and slows to 5 mph, he/she may still running, although at a slower pace. In this situation, however, the frequency detected will be altered.

In one embodiment, step quantification may be determined absent linear combinations, such as for example, by identifying peaks as discussed above. The estimate (which may have been adjusted via block 1008) may be used to establish a search range for bounce peak and/or arm swing peak within the data (See, e.g., block 1012).

Block 1014 may be implemented to identify a sub-group (or sub-groups) of peaks within the frequency data to utilize in the determinations of step quantification. In one embodiment, a FFT is performed and peaks in the FFT spectrum may be identified, such as with the thresholds and/or derivative around the peak. The performance of the FFT may occur before, during, or after initiating frequency estimation processes, such as one or more processes described in relation to FIG. 10. In further embodiments, the FFT may utilize one or more threshold and derivatives derived from one or more process of flowchart 1000. In on embodiment, a specific peak (or peaks) within the data (such as for example, data obtained within the first buffer and/or data obtained during first time frame) may be utilized. This may be conducted based upon determining that linear combination cannot be used. In one embodiment, "bounce peaks," "arm swing peaks," and/or other peaks may be identified. For example, many users "bounce" upon landing their feet when running. This bounce may provide frequency peaks within the data. Other peaks (and/or valleys) may be present within the sensor data. For example, many users often swing their arms in a predictable manner during running and/or walking to provide "arm swing peaks". For example, arms usually swing along an anterior/posterior axis (e.g., front to back). This frequency may be about half the frequency of the "bounce peaks". These peaks, however, may each vary independently, based upon, for example, the individual, the type of motion, the terrain, and/or a combination thereof.

Figure 12A:
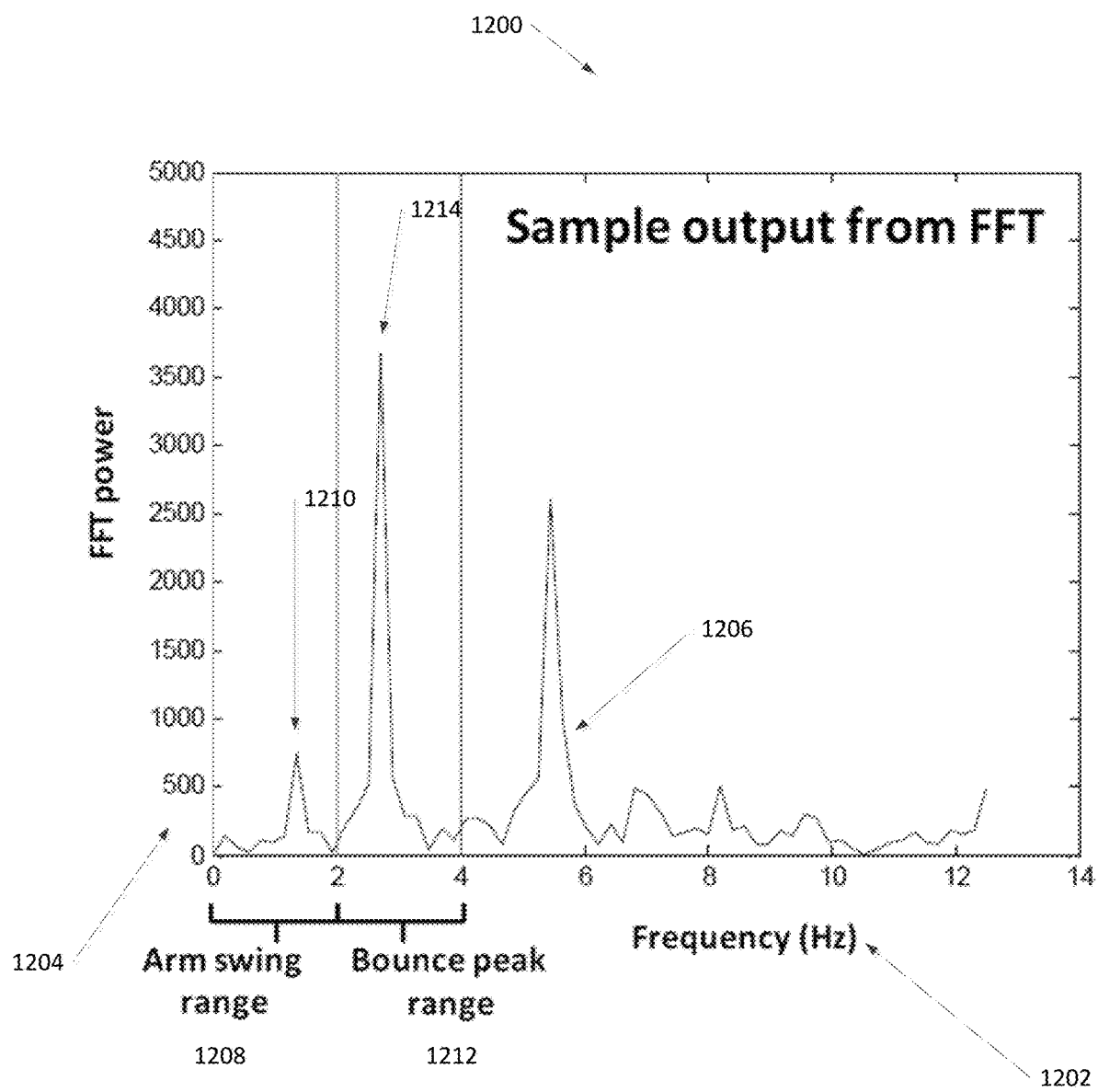
FIGS. 12A and 12B show a graph illustrating a sample FFT output. Specifically.

FIG. 12A shows graph 1200 of an example FFT output of sensor data, such as multi-axis accelerometer data. Graph 1200 shows the frequency in Hertz (Hz) along x-axis 1202 and FFT power along y-axis 1204. Line 1206 plots the frequency (along x-axis 1202) against the power (along y-axis 1208), wherein the magnitude or maximum height along the y-axis 1204 provides the maximum FFT power for a peak. The peak magnitude indicates the relative strength of the frequency, and may be used as an indicator whether a person is stepping. Those skilled in the art will appreciate that graph 1200 is not required to be generated or displayed, but rather is illustrated herein to demonstrate aspects of this disclosure.

As further seen in FIG. 12A, arm swing range 1208 is shown between about 0 and 2 Hz along x-axis 1202 and comprises arm swing peak 1210. Bounce peak range is shown at about 2-4 Hz along the x-axis 1202 and comprises bounce peak 1214. Thus, in the illustrated example, the frequency of the bounce peak 1208 within bounce peak range is generally twice the frequency of the arm swing peak. Thus, systems and methods may identify peaks (and/or valleys) based upon the established thresholds. In this regard, computer-executable instructions of one or more non-transitory computer-readable mediums may be executed to determine if a threshold quantity of peaks are located within the range (either fixed or dynamically determined). If no peaks within the range are located, that buffer may be emptied (or otherwise not utilize that data in step counting determinations). In this regard, the peaks may refer to the frequencies may be measured by those with the highest quantity of occurrences and/or highest absolute value.

Figure 12B:
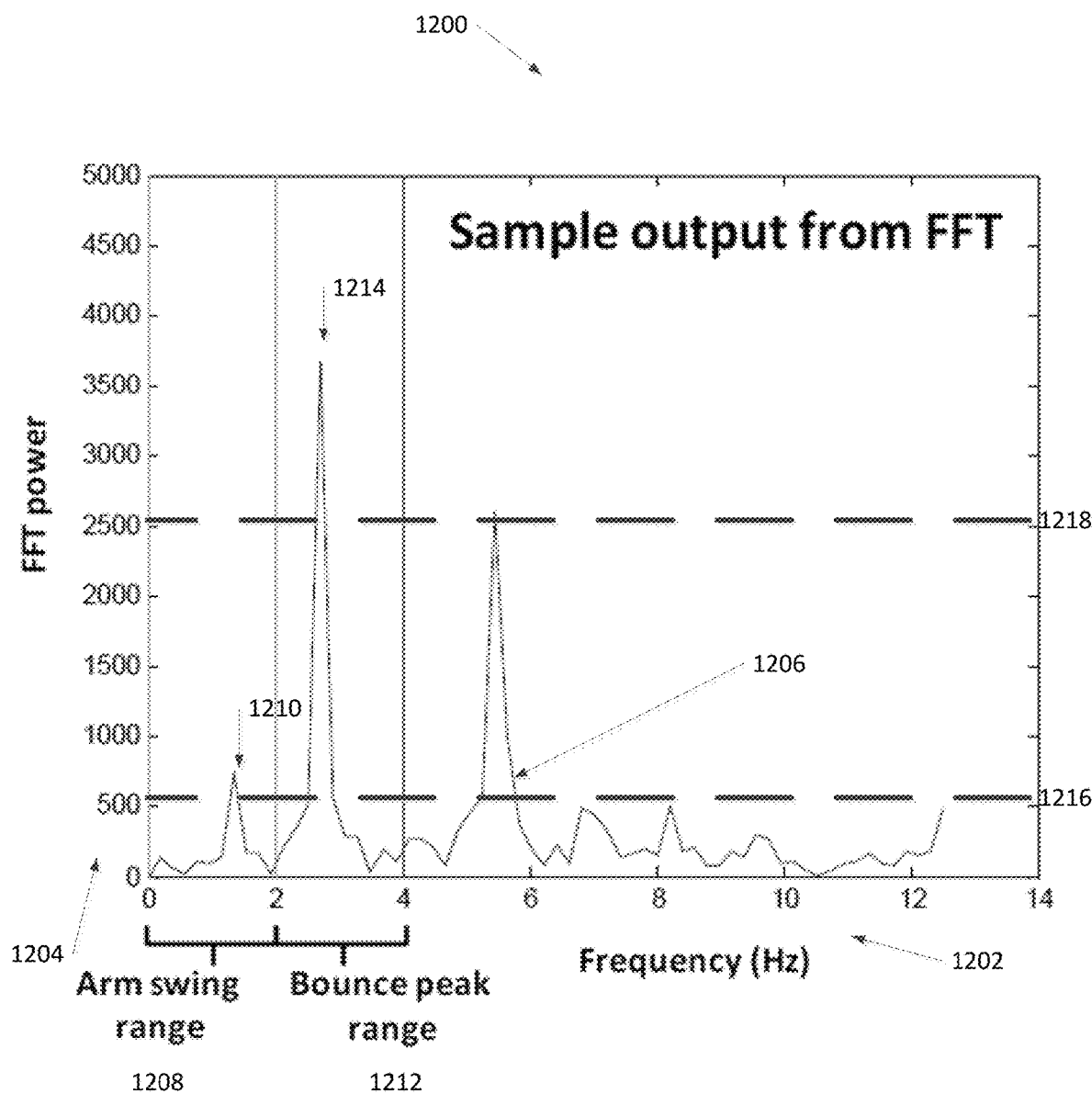

Certain embodiments may determine whether peaks (e.g., arm swing peak, bounce peak, and/or any other peak) meet a threshold. In one embodiment, a threshold of the frequency power within the constrained search range may ensure that the frequency is not simply noise and that it is large enough to be considered an activity (such as, for example, walking or running) In yet another embodiment, an overlapping window strategy may be utilized. For example, FFT windows may be analyzed in an overlapping fashion to make sure short term duration steps are counted. FIG. 12B shows graph 1200 as substantially shown in FIG. 12A, however, further includes arm swing threshold 1216 and bounce threshold 1218. As shown, peaks within arm swing range 1208 (between 0-2 Hz) may only be counted if their magnitude meets a threshold of FFT power (e.g., threshold 1216 is at about 500 as shown on the y-axis 1204).

Likewise, in certain embodiments, peaks within bounce peak range (2-4 Hz) may only be counted if their magnitude meets a threshold (such as bounce threshold 1218, which is at about 2500 as shown on the on the y-axis 1204). In certain embodiments, peaks that meet or exceed a threshold may be counted as steps (see, block 1016). The steps may be incremented for a set time, such as the duration of the FFT analysis window. Certain embodiments may continue incrementing with overlapping windows. In one embodiment, steps may be quantified for each sample buffer or a certain portion (e.g., 25%) of the analysis buffer and if the threshold is met, then steps may be counted for the specific sample buffer or portion of activity buffer. If, however, the threshold for that sample buffer or portion is not met, then steps for the remaining portion of the activity buffer (or specific surrounding samples) is determined based upon the step frequency. For example, if analysis buffer comprises 4 sample buffers and only the first 3 have steps, then the step count for ¾ of that analysis buffer may be based upon the previously selected step frequency.

Further aspects relate to selecting which peaks, if any, are utilized. In accordance with one embodiment, systems and methods may select which peaks are to be utilized in quantifying steps despite the fact that the located peaks are deemed valid or meet a threshold. As discussed above, bounce data from foot contact may be more reliable arm swing data in some circumstances. Equally, arm swing data may provide more accurate results in other embodiments. In still further instances, using both peaks (and/or others) together to derive a range of data may provide the best results. Embodiments disclosed herein relate to systems and methods that may be used on a portable device configured to be worn on an appendage (such as an arm or leg) to collect activity data and determine which peaks to utilize in quantifying steps (and possibly in further embodiments, activity type and/or energy expenditure). In this regard, combinations of various peaks may be used to determine specific activities of the athlete. In certain embodiments, systems and methods may be configured to dynamically determine whether to use bounce peaks, such as for example peak 1214 or arm swing peaks, such as peak 1210. The determination may be updated in substantially real-time (such as every 0.5 seconds, 1 second, 2 seconds, 4 seconds, etc.) and based upon the activity data.

Figure 13A:
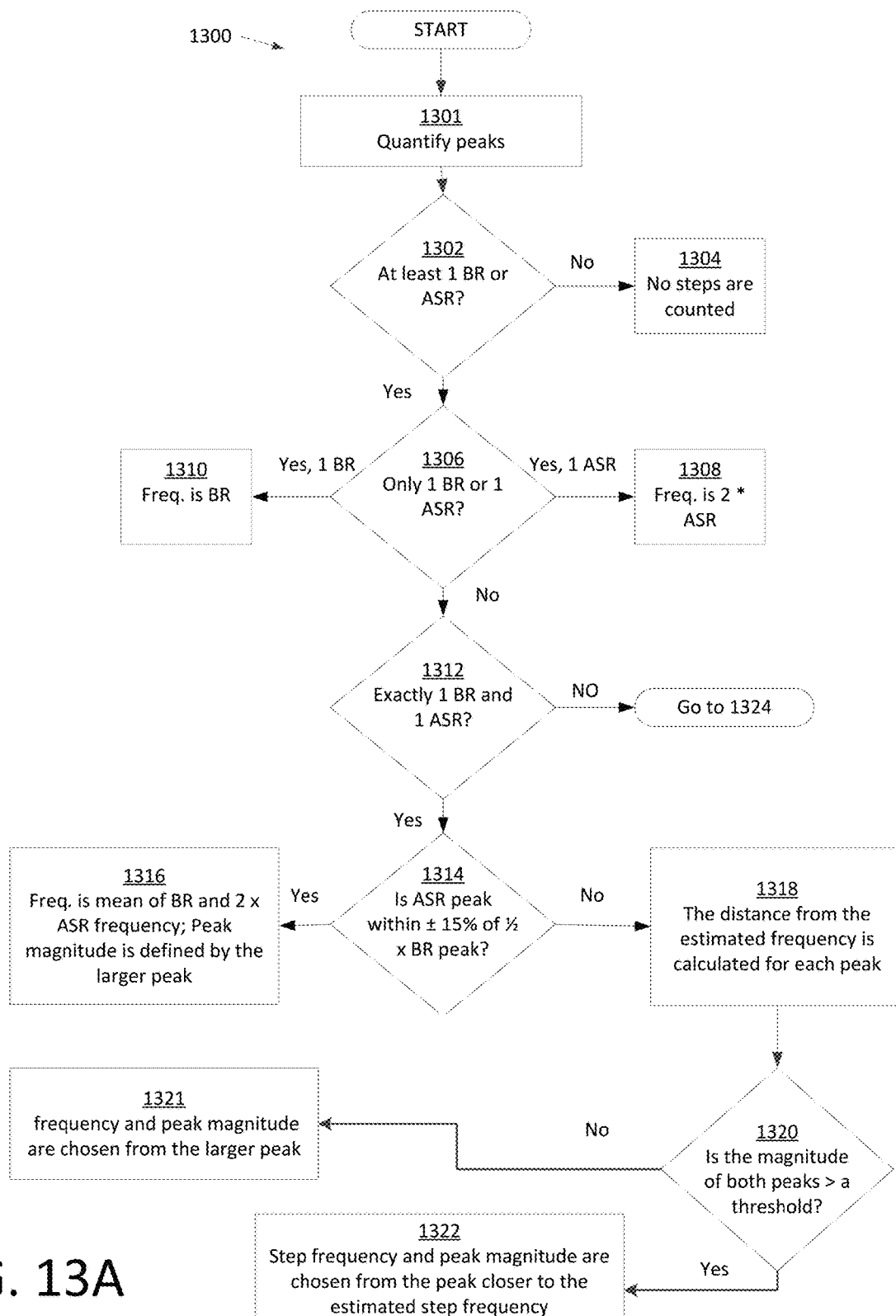
FIGS. 13A and 13B show example flowcharts that may be implemented in determinations of whether to utilize arm swing frequency, bounce frequency and/or other frequencies in accordance with one embodiment.

FIG. 13 shows example flowcharts that may be implemented to determine whether to utilize arm swing frequency or bounce frequency in accordance with one embodiment. As shown in FIG. 13, the systems and methods may be implemented to select relevant frequency peaks out of the illustrative FFT output to determine which data provides the most accurate results (e.g., a which frequency from an FFT analysis of accelerometer data should be utilized). In certain embodiments, step frequency may be used in the generation of a step count for the period of time represented by the FFT spectrum.

In one embodiment, the "relevant" peaks may include arm swing peaks and bounce peaks. Block 1301 may be implemented to quantify the number of identified peaks within the corresponding search range. Thus, the bounce peaks located in the frequency estimation for the bounce range ("BR") (see, e.g., range 1208 comprising frequencies between 0-2 Hz of FIG. 12A) may be quantified and the arm swing peaks located in the frequency estimation for arm swing range ("ASR") (e.g., range 1212 comprising frequencies between 2-4 Hz of FIG. 12A) may also be quantified. In certain embodiments, the quantity of identified peaks (and/or quantity of specific peaks identified) may be utilized to determine which of the estimated step frequencies (e.g., determined by the ASR, BR or peaks in other ranges) may utilized. For example, decision 1302 may determine whether there is at least 1 peak in the BR or at least 1 peak in the ASR. If not, block 1304 may be implemented to register that no steps were performed in the specified range. If, however, there is at least 1 BR or at least 1 ASR peak at decision 1302, decision 1306 may be implemented to determine if there is only 1 BR peak (and zero ASR peaks) or alternatively, if there is 1 ASR peak (and zero BR peaks). If it is determined that there is only the 1 ASR peak, then block 1308 may be implemented to mark the step frequency at 2*ASR frequency. Alternatively, if it is determined that there is the one BR peak, then block 1310 may be implemented to mark the step frequency as corresponding to the BR frequency. As a third alternative, if there are more than only 1 ASR or only 1 BR in absence of each other, then decision 1312 may be implemented. Before discussing decision 1312, it is worth noting to the reader that FIG. 13 (and other flowcharts provided herein) include several decisions, such as for example, decisions 1302, 1306, 1312 and 1314. Those skilled in the art with the benefit of this disclosure will readily appreciate that one or more decisions may be grouped into a single decision and/or placed in different order, such as incorporating decision 1304 within decision 1302. Thus, the use of a plurality of decisions in the current order is merely for illustrative purposes.

One or more processes may determine whether there are exactly 1 BR peak and 1 ASR peak (see, e.g., decision 1312). If not, block 1324 (which is discussed below) may be implemented. If so, however, decision 1314 may be implemented to determine whether the ASR peak is within a set range of the BR peak. In one embodiment, decision 1314 may determine whether the ASR peak is within +/−15% of the ½*BR peak. If so, block 1316 may be implemented to determine that the step frequency is the mean of the BR peak and 2× the ASR frequency.

If, however, the ASR peak and the BR peak are not within the identified range threshold, then block 1318 may be implemented to calculate the distance from the estimated frequency for each peak. One or more processes may then determine whether the magnitude of at least one of the peaks is greater than a threshold. For example, decision 1320 may be implemented to determine if the magnitude of both peaks are greater than a threshold. If the threshold(s) of decision 1320 are not satisfied, block 1321 may be implemented to select the frequency and magnitude of the larger of the two peaks. If the magnitude of the peaks, however, are greater than a threshold, then step frequency and peak magnitude may be chosen from the peak closer to the estimated step frequency (e.g., block 1322).

Figure 13B:
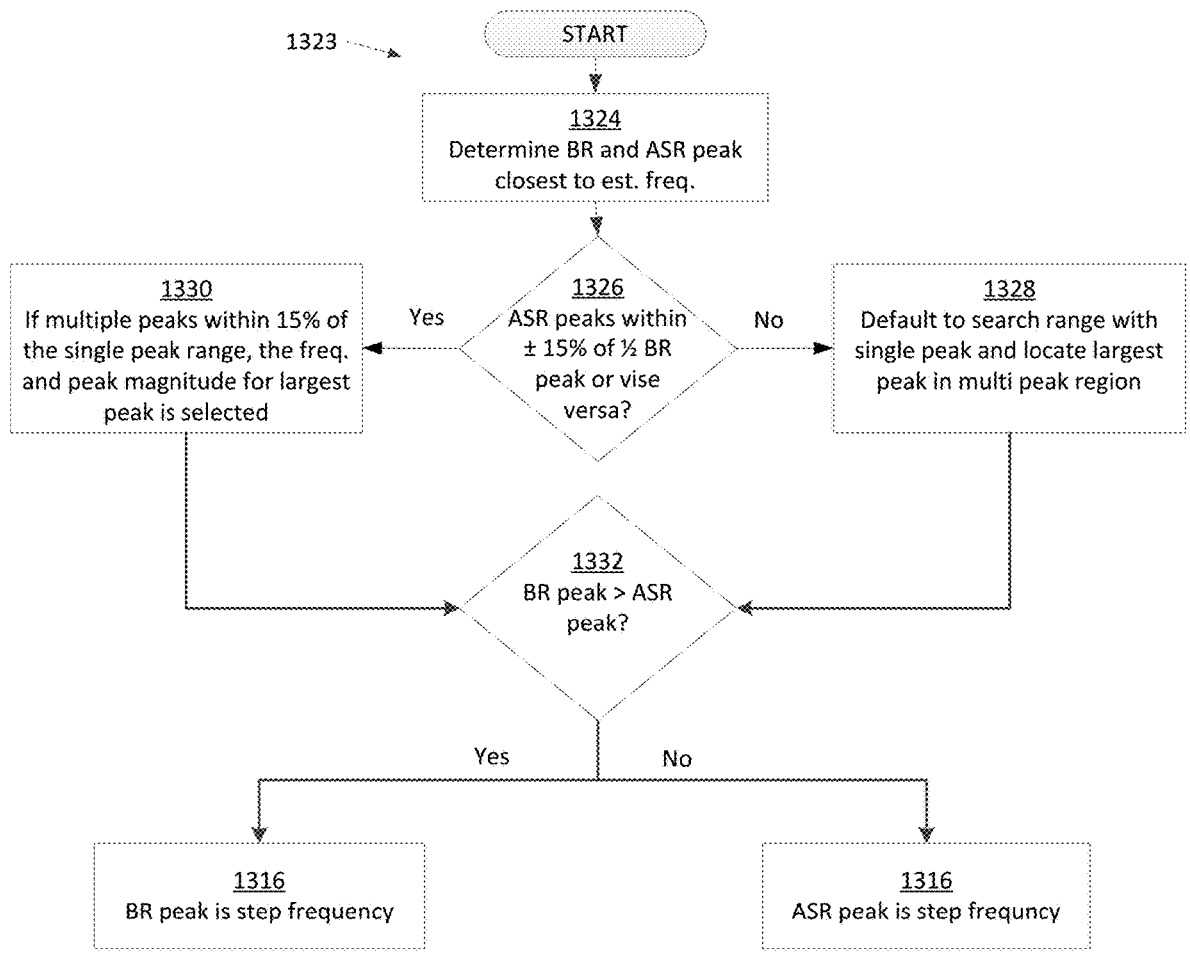

Looking to FIG. 13B showing flowchart 1323, systems and methods may be configured to determine the step frequency when there are more than 1 BR peak and more than 1 ASR peak in the search range. In one embodiment, block 1324 may be utilized determine the step frequency when there are more than 1 BR peak and 1 ASR peak in the data. Block 1324 may be implemented upon determining that there is not exactly 1 BR peak and 1 ASR peak at decision 1312 of FIG. 13A, yet in other embodiments, block 1324 is independent of decision 1312 and/or FIG. 13A. Block 1324 may determine peak proximity to an estimated frequency, such as the frequency estimated by a frequency estimator (see, e.g., block 1002 and flowchart 1000). In one embodiment, the BR peak and ASR peak closest the estimated frequency are determined. Decision 1326 may be implemented to determine whether at least one identified ASR peak is within a set range of the BR peak and/or whether at least one identified BR peak within a set range of the ASR peak. In one embodiment, decision 1326 may determine whether the ASR peak is within +/−15% of the ½*BR peak or whether the BR peaks are within +/−15% of ½*ASR peak.

If it's determined at decision 1326 that the threshold range set is not met, then block 1328 may be initiated to default to a search range with a single peak and locate the largest peak in the multi-peak region. Alternatively, block 1330 may be implemented if a criterion set forth in decision 1326 is satisfied. In one embodiment, if there are multiple peaks within the set range set forth in decision 1326 (e.g., 15%) of the single peak range, block 1330 may be implemented to select the frequency and peak magnitude for the biggest peak. Decision 1332 may be implemented to determine which of the identified peaks are larger. For example, decision 1332 may determine whether the BR peak is larger than the ASR peak (or vice versa). Decision 1332 may merely determine which of the BR peak and the ASR peak is larger. In one embodiment, the larger of the two peaks may be selected as the step frequency (see, e.g., blocks 1334 and 1336).

FIG. 14 depicts a flowchart 1400 which may represent one or more processes to compare one or more calculated attributes from received sensor data with one or more expert models. Accordingly, FIG. 14 may be described as an expert selection module. Those of ordinary skill in the art will readily understand statistical analysis methodology described as a mixture of experts. Accordingly, in one implementation, an expert may be a model that may be used to estimate an output value. In one example, an output value may be an estimation of oxygen consumption associated with one or more activities being performed by a user.

As described briefly in relation to FIG. 6, in one example, 16 experts (models) may be stored in a device, such as device 112, 126, 128, 130, and/or 400. Additionally, there may be a number of attributes (otherwise referred to as weights) stored in association with each expert. In one example, 20 attributes may be compared with 20 weights associated with each expert model, and wherein said attributes are calculated according to those processes described in relation to FIGS. 9A-9E and FIGS. 17A-17E, and the like.

In response to receipt, at block 1402, of calculated attributes, weights associated with each stored expert model may be selected (block 1404). For each expert model, a probability may be calculated that said expert model is the best match for those received attributes, wherein the best match represents a model that will predict with highest accuracy an output of the model, given the calculated attribute inputs. In one example, block 1406 may represent one or more processes to calculate a probability that an expert is a best match for received attributes using a Softmax regression function, and according to a "mixture of experts" methodology, and the like.

Accordingly, given, in one example, 20 input attributes calculated from sensor data received from an accelerometer, and indicative of an activity being performed by a user, those 20 attributes may be compared to an equal number of weights associated with each of the models stored in the energy expenditure system. A calculated Softmax regression may return a probability value associated with each stored model, wherein each probability value represents a likelihood that the associated model will give a best available estimate of, in one example, a volume of oxygen being consumed by a user. For example, an energy estimation system may store four models (experts). Accordingly, using attributes calculated from received acceleration sensor data, a Softmax regression may be calculated for each of the four models. In one example, this Softmax regression may calculate a probability for each of the four models. Accordingly, the model corresponding to the highest calculated probability is the model to be used to give a best available estimate of a volume of oxygen being consumed by a user. In one implementation, a Softmax regression may be calculated using the formula:

$$p_i = \frac{e^{m_i^T k}}{\sum_k e^{m_i^T k}}$$ (Softmax regression equation)

As described in the Softmax regression equation above, p represents the probability that model i is the best model, from k different models, to use to predict a volume of oxygen consumption, given the vector of input attributes, symbolized by vector x, calculated from sensor input values. Furthermore, is a vector of weights associated with model i.

Block 1406 may produce one or more outputs representing one or more probabilities that an associated expert model represents a best-much for calculated attribute values. Block 1408 may select an expert with a highest probability from those outputs of block 1406. Accordingly, block 1408 may estimate an output using the selected expert, and wherein the output may be an estimated volume of oxygen consumption by a user, and based on one or more activities being performed by the user, and the like.

Further aspects relate to systems and methods for calculating one or more other metrics, such as the athlete's speed, distance, and or other one or more parameters. In one embodiment in which speed is an attribute being calculated, a speed calculation module may be provided. Provided with the relevant attributes for the window of interest, systems and methods may be implemented to determine whether to calculate speed for one or more windows of data. In one implementation, if a data window is determined to contain walking or running data, the relevant attributes may be utilized, such as by being sent to a speed and distance module, to calculate speed and distance. Thus, it goes from the foregoing that certain aspects of this disclosure relate to determinations of speed or distance that comprises categorizing athletic data. As discussed above, certain aspects relate to calculating energy expenditure values without categorizing the athletic data into activity types (walking, running, basketball, sprinting, soccer, football, etc.), however, categorizing at least a portion of the same data utilized to calculate energy expenditure for the calculation of other metrics, such as for example, speed and/or distance is within the scope of this disclosure. Speed (or another parameter determined from the categorization of athletic data may) be computed from the same attributes utilized for the determination of energy expenditure values. In this regard, the same exact set of attributes may be used, however, in yet another embodiment, a sub-set of the same attributes may be used; and in yet additional embodiments, there may be only a single common attribute value utilized in the determination of two different metrics (such as, for example, speed and/or energy expenditure). In one implementation, speed (or another metric) may be determined from at least a portion of data derived from the determination of energy expenditure values.

Figure 15A:
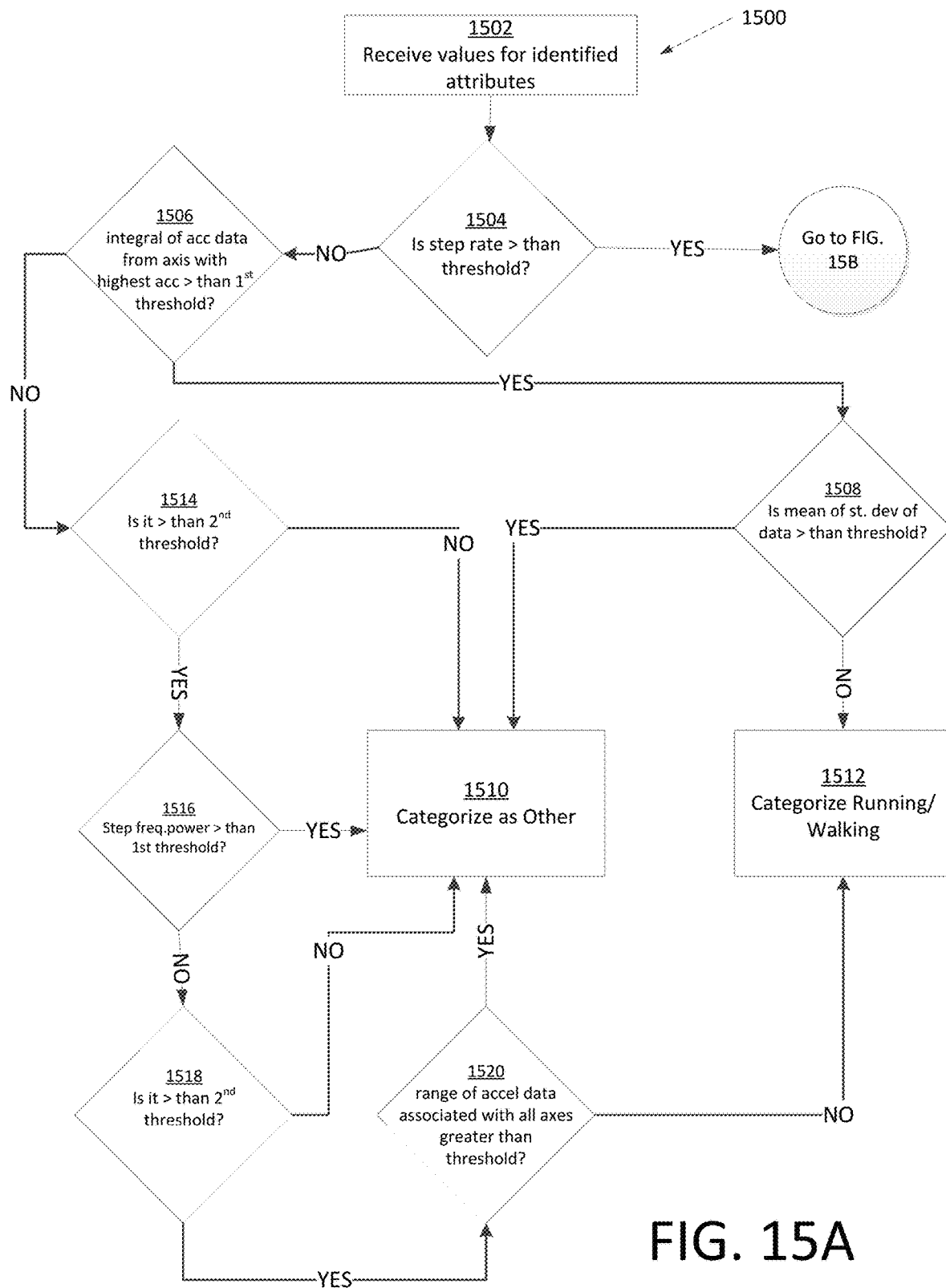
FIGS. 15A-15C depict flowchart diagrams that may be implemented to categorize an athlete's activity in accordance with one embodiment.
Figure 15B:
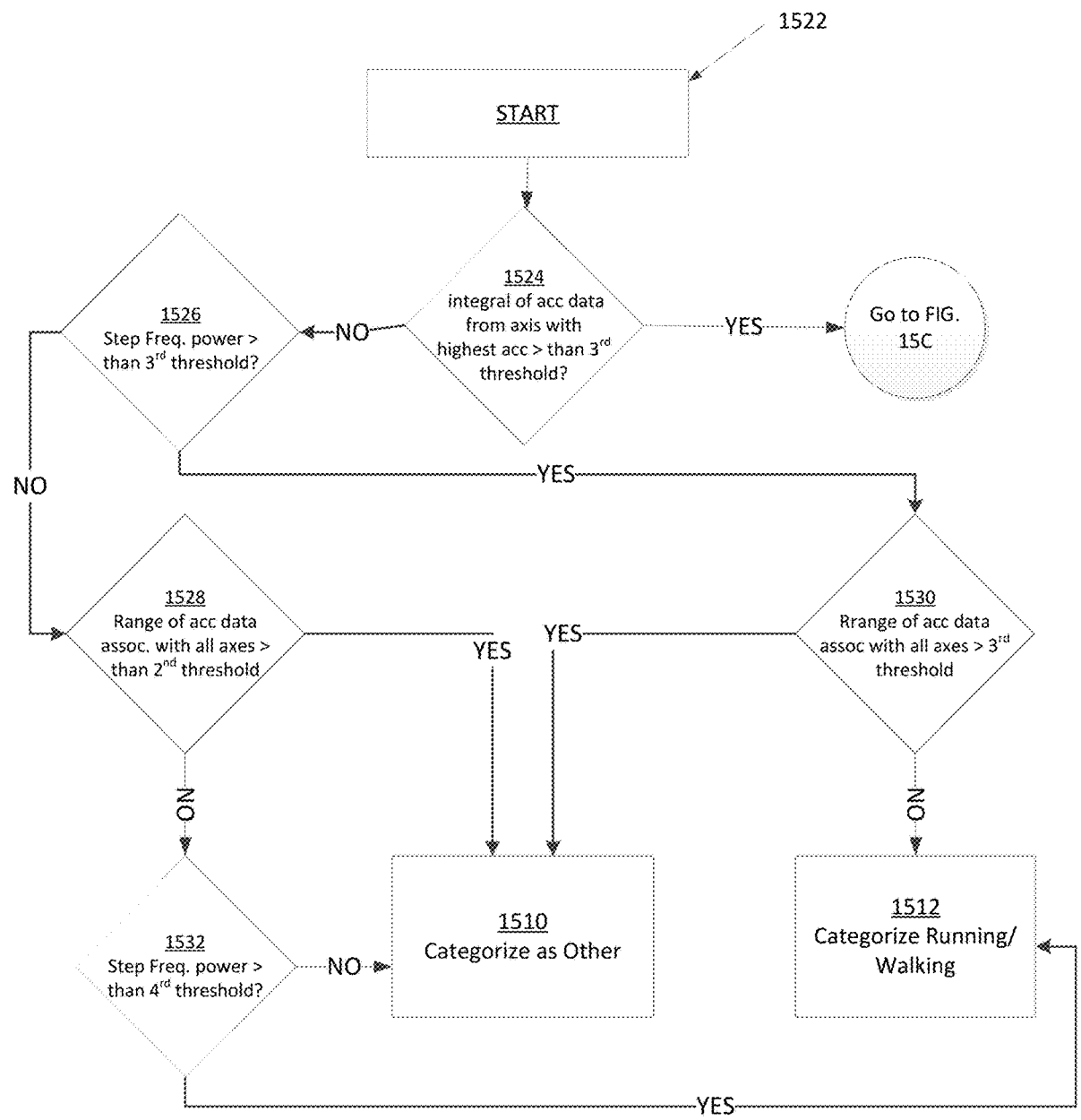
Figure 15C:
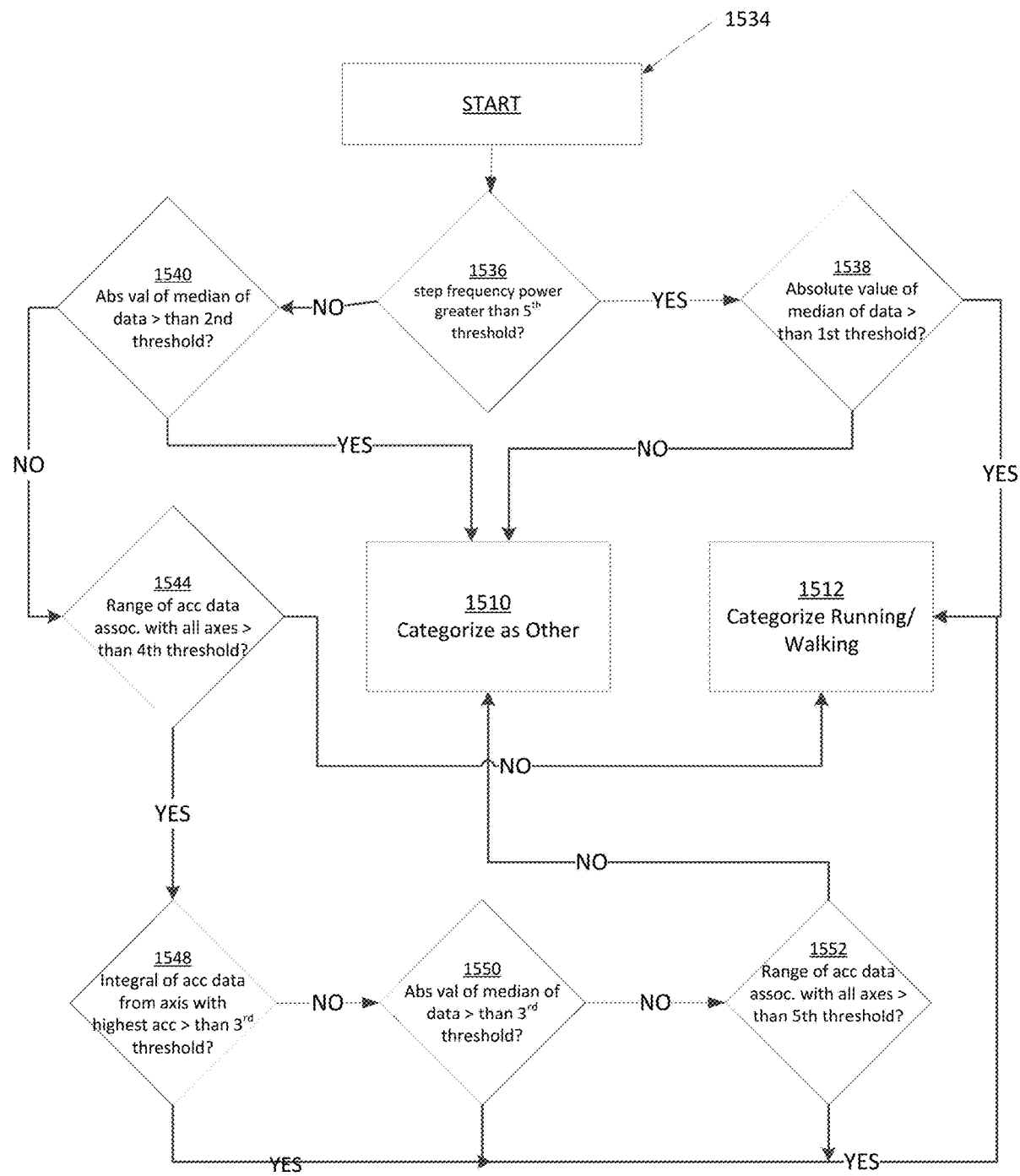
Figure 16:
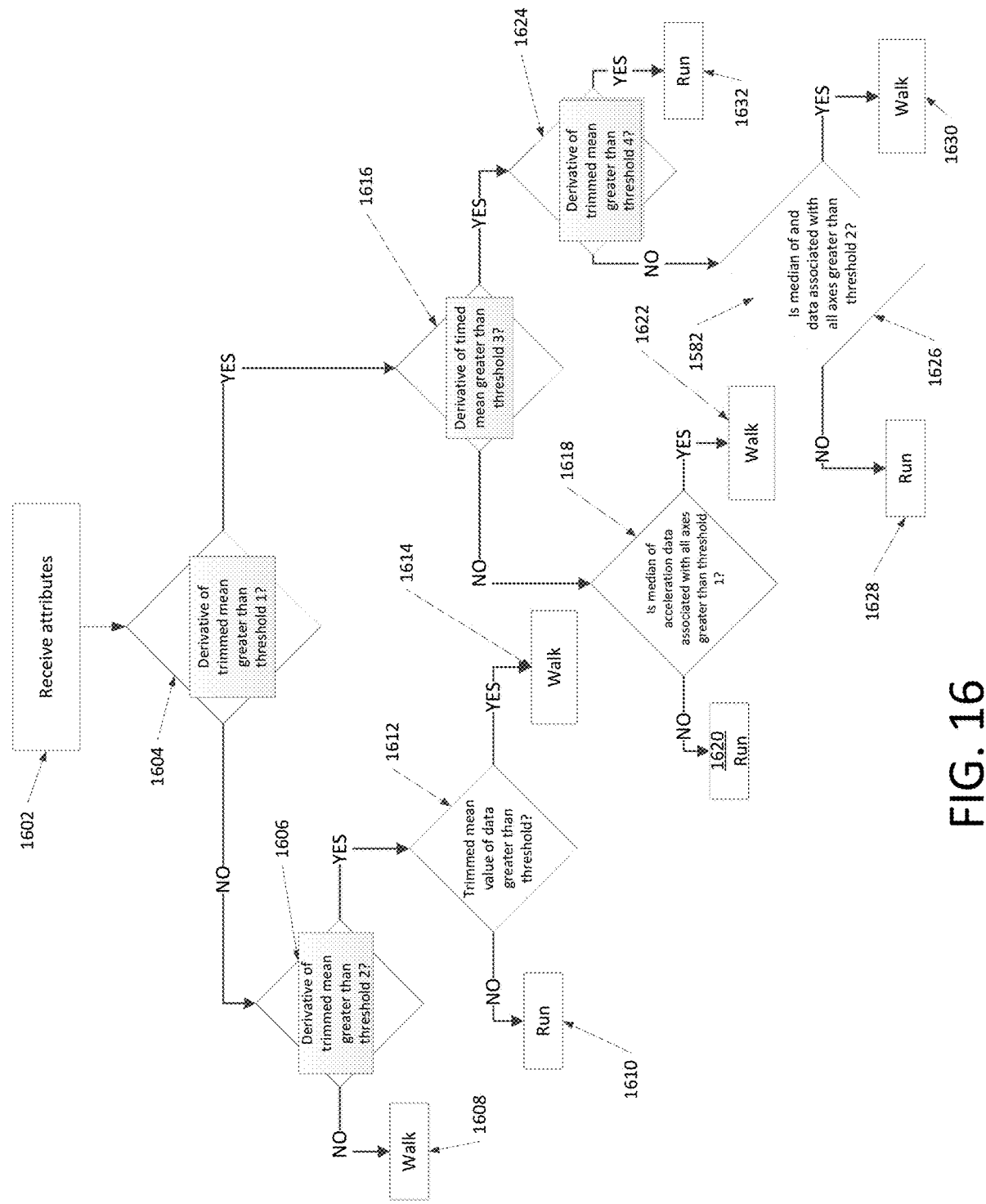
FIG. 16 is a flowchart that may be implemented to categorize an certain activity as either walking or running in accordance with one embodiment.

FIGS. 15 and 16 are flowcharts showing example processes that may be utilized in categorizing the athlete's activity (such as, for example, into categories of: "walking", "running", or "other") based upon at least a portion of the attributes utilized in the calculation of energy expenditure values. Although example embodiments described herein utilize the categories "walking", "running" and/or "other", those skilled in the art will appreciate that this is for illustrative purposes and other categories are within the scope of this disclosure. Further, although the categories of FIGS. 15 and 16 are provided in the exemplary context of determining speed and/or distance, this is not a requirement. In this regard, categorization of activity data may be performed independently of any determinations of speed and/or distance.

Looking first to FIG. 15, one or more processes may be utilized to first determine whether the data is to be considered within a first sub-group (e.g., inclusive of walking and running) or, alternatively, within a second sub-group (e.g., other than walking or running) In one example, one or more processes may be utilized to determine whether data is to be considered within a linear travel motion sub-group, or alternatively, a linear motion sub-group. This linear travel motion sub-group may, in one example, correspond to walking and/or running. Furthermore, those of ordinary skill will understand that the linear travel motion sub-group includes substantially linear motion, such as that associated with walking or running, and as opposed to that comparatively random movement of a person participating in a team sport, such as basketball, soccer, ice hockey, and the like. Accordingly, running and walking may be referred to/categorized as "linear travel motion" in comparison to the stop-start/comparatively more intermittent nature of user motion while participating in other athletic activities, such as team sports. In another example, however, the linear travel motion of running or walking may include running and/or walking around a track, wherein certain periods of running and/or walking may be considered circular motion, and the like.

Values for attributes (such as one or more of the attributes disclosed herein and/or known in the art) may be received (e.g., see block 1502). In one embodiment, a 128 sample window of acceleration data at 25 Hz may be utilized. In one embodiment, a wrist-mounted accelerometer, which may be a multi-axis accelerometer, may be utilized to capture data.

Step rate may be a criterion utilized to categorize the activity data. Step rate may be an attribute utilized in the determination of energy expenditure, derived from an attribute, and/or independently derived for categorization purposes. In certain embodiments, the step rate may be compared to one or more thresholds (see, e.g., block 1504 of FIG. 15A). As used herein, recitation of a second, third or any subsequent threshold (or other values) is merely for descriptive purposes to distinguish from earlier-mentioned thresholds and not limited to specific ordering and/or quantity of threshold or ranges. Specific attributes and ordering of the attributes may be based upon whether the step rate meets designated thresholds. For example, if the step rate does not exceed a first threshold (see, e.g., block 1504), it may then be determined whether the integral of the accelerometer data from the axis with highest acceleration values is greater than a 1st threshold (see, e.g., block 1506), wherein if the if the step rate exceeds the first threshold for step rate, it may then be determined whether the integral of the accelerometer data from the axis with highest acceleration values is greater than a $2^{nd}$ threshold (as opposed to the first threshold) set for that same attribute (see, e.g., decision block 524 of FIG. 15B).

The remainder of FIG. 15A will be described in the context of the determination that the step rate met the first threshold, and FIG. 15B will be described in the context of the step rate not meeting the first threshold, however, those skilled in the art will readily understand that such an implementation is merely one example. Utilizing data from a single axis, such as the axis with the greatest magnitude (e.g., decisions 1504 and 1524), may be beneficial in certain circumstances to restrain the amount of data needed to be analyzed for reliable determinations.

If the integral of the accelerometer data from the axis with highest acceleration magnitude is greater than a 1st threshold set for that attribute, variation of the data may be examined to determine categorization of activity. As one example, the mean of the standard deviation ("std. dev.") of the data may be considered (see, e.g., block 1508). In one embodiment, if the mean of the std. dev. exceeds a threshold, then the data may be too inconsistent to be categorized as "walking" or "running". This is not to suggest that the user's activity did not include walking or running, for example, the user may be playing defensive maneuvers during a basketball game, however, categorizing it as "walking" or "running" may not be the most accurate category. As one example, merely categorizing a defensive basketball's movements as "walking" and attempting to determine distance from relatively smaller sidesteps may not be preferable in certain implementations. In one embodiment, if the mean of the std. dev. exceeds a threshold, the data may be categorized as a non-walking and/or non-running category. For example, it may be categorized as "other." (see block 1510). Alternatively, if the mean of the std. dev. does not exceed the threshold, it may be classified as containing "running" and/or "walking" (see, e.g., block 1512). As explained in more detail below with reference to FIG. 16, further analysis may be performed to designate the data as either "running" or "walking."

Returning to exemplary block 1506, the integral of the accelerometer data from the axis with highest acceleration values may not be greater than the 1st threshold set for that attribute, therefore, it may be determined whether the integral exceeds a second threshold (see, block 1514). In certain embodiments, the second threshold may be quantitatively lower than the first threshold (e.g., a smaller value—which may be in one example, indicative of a lower amount of acceleration by a user). If the integral does not meet the second threshold, the data may be categorized as not being running or walking data (see, block 1510). If, however, the second integral threshold is met, step frequency power ("step freq. power") may be utilized to categorize activity data. For example, if the step freq. power exceeds a first threshold, it may be categorized as "other" (see, e.g., decision 1516 going to block 1510). If it does not exceed the first threshold, it may be compared to a second threshold (e.g., decision 1518). A negative determination at decision 1518 may result in categorizing the data as categorized as not being walking or running data, whereas an affirmative finding may result in further analysis (see, e.g., decision 1520). In one embodiment, the range of sensor data (such as accelerometer data associated a plurality of axes—such as x, y and z axes) may be compared with a threshold (e.g., block 1520). In one embodiment, if the range threshold is not met, the data may be classified as running or walking, whereas if the threshold is met, the data may not be classified as walking or running.

FIG. 15B will be described in the context of the step rate not meeting the first threshold (see, e.g., decision 1504 of FIG. 15A), however, those skilled in the art will appreciate that one or more aspects of FIG. 15A, including the utilization of the first threshold of block 1504, may be omitted from one or more processes. In one embodiment, the entirety of flowchart 1500 of FIG. 15 may be omitted. In one such embodiment, FIG. 15B may show the initial stages of a categorization function.

As discussed above, certain embodiments may utilize the data from an axis with the highest magnitude. As one example, it may be determined whether the integral of the accelerometer data from the axis with highest acceleration magnitude values is greater than a threshold set for that attribute (see, e.g., decision 1524). In one embodiment, the "$3^{rd}$ threshold" of decision 1524 may be indicative of less movement along the respective axis than set by the first and/or second thresholds. If the threshold is not exceeded, step freq. power (e.g., a third threshold of step freq. power at decision 1526) may be utilized. In one embodiment in which at least three thresholds for step freq. power are utilized in an overall process for categorizing activities, the third threshold (e.g., the threshold utilized at decision 1526) may be a value that is numerically "in-between" the first and second threshold values. In one embodiment, the first threshold value may be greater than the third threshold value;

however, the second threshold value may be less than the third value. Yet, in other embodiments, the threshold value may be greater or less than either one or more other thresholds for this attribute.

In one embodiment, the range of sensor data (such as accelerometer data) associated a plurality of axes (e.g., x, y and z axes) may be compared with one more thresholds (e.g., decisions 1528 and 1530) based upon whether a threshold of decision 1526 is not met. In one embodiment, if a second threshold (which may be different than the first threshold of decision 1520) may be about half of a third threshold for this attribute. In one embodiment, one of the thresholds may be within +/−10% of another threshold. In one embodiment, the threshold of decision 1530 is the highest threshold for that attribute. If the thresholds of decisions 1528 or 1530 are met, the data may not be categorized as running or walking (See, decisions 1528 and 1530 going to block 1510 labeled "other"). A determination that the third threshold is not met (e.g., at decision 1530), may result in classifying the data as running or walking, whereas for the second threshold (see decision 1528), further analysis may be conducted if the threshold is not met. In one embodiment, if the threshold of decision 1528 is not met, step freq. power (e.g., the fourth threshold of step freq. power at decision 1532) may be utilized. The threshold of block 1532 may be 10%, 5% or less of any other step freq. power threshold utilized. If the threshold of block 1532 is met, the data may be categorized as walking or running, yet if the threshold is not met, the data may be classified as not walking or running.

FIG. 15C may be viewed in the context of FIGS. 15A and 15B, in which a first step count threshold was not met (see, e.g., decision 1504 of FIG. 15A) and/or an integral of sensor data from the axis with the highest magnitude was met (e.g., decision 1524 of FIG. 15B), however, those skilled in the art will appreciate that one or more aspects of FIG. 15A and/or FIG. 15B, including the utilization of the specific thresholds may be omitted from one or more processes conducted in relation to FIG. 15C. In one embodiment, the entirety of flowcharts 1500 of FIG. 15 and/or 1522 of FIG. 15B may be omitted. In one such embodiment, FIG. 15C, inclusive of any portion of flowchart 1534, may show the initial stages of a categorization function.

In one implementation, a determination may be made whether a step freq. power threshold is met (e.g., at decision 1536). In one embodiment, the threshold is different than the previous four step freq. power thresholds discussed in relation to FIGS. 15A and 15B. A negative finding may result in a subsequent determination whether the absolute value ("abs val") of the median of the data is greater than a first threshold (e.g., decision 1538), whereas an affirmative determination may result in a subsequent determination weather the abs val of the median of the data meets a second threshold (e.g., decision 1540).

Looking first to decision 1538, upon determining that the abs value threshold is met, the data may be classified as running or walking, whereas if the threshold is not met, the data may not be classified as walking or running (such as for example, placed within an "other" categorization). At block 1540, however, if the relevant abs value threshold is met, the data may be categorized data as not being running or walking, whereas a negative finding may result in further analysis.

In one embodiment, if a threshold of decision 1540 is not met, the range of sensor data (such as accelerometer data) associated a plurality of axes (e.g., x, y and z axes) may be compared with one more thresholds (see, e.g., decision 1544). In one embodiment, it may be a fourth range threshold that is different than the other thresholds (such as optional thresholds of decisions 1528 and 1530). In one embodiment, if the threshold of block 1544 is not met, the data may be categorized as running or walking (See, decision 1544 going to block 1512). If the threshold of decision 1544 is met, then an integral threshold, such as from the axis with the highest magnitude may be utilized (see, e.g., decision 1548), whereas if the threshold is met, then the data is classified as walking or running data, and wherein if it's not met, then further analysis may be conducted.

In accordance with one implementation, it may be determined whether the absolute value ("abs val") of the median of the data is greater than a threshold (e.g., decision 1550). The threshold may be less than one or more other abs val thresholds, such as thresholds utilized in decisions 1538 and/or 1540). An affirmative determination at decision 1550 may result in the data being categorized as running or walking A negative finding may result in considering the range of data across multiple axes. In one embodiment, it may be determined whether the range of sensor data (such as accelerometer data) associated a plurality of axes (e.g., x, y and z axes) meets a threshold (e.g., decision 1552). In one embodiment previously employing a first range threshold (such as, for example, decision 1544), decision 1552 may employ a second range threshold that is greater than the first range threshold. In accordance with one implementation, if the threshold of decision 1552 is met, the data may be classified as running or walking, whereas if the threshold is not met, the data may not be classified as walking or running.

FIG. 16 is a flowchart showing an example implementation of classifying sensor data as either walking or running (as opposed to, for example, a single category that contains both). Looking first to flowchart 1600 of FIG. 16, one or more processes may be utilized to determine whether the data should be categorized as either "walking" or "running". In other embodiments, additional options may be available. Data, such as attribute values, may be received at block 1602. Attribute values received at block 1502 may be the same attribute values received at block 1502 and/or utilized to calculate other metrics, such as energy expenditure, heart rate, and/or others. In this regard, the attributes utilized in block 1602 may include one or more of the attributes disclosed herein and/or known in the art. In accordance with one embodiment, attribute values of data previously pre-screened or otherwise deemed to contain walking or running data may be utilized. For example, one or more processes set forth in FIGS. 15A-15C may be used to categorize at least a portion of the received data as containing walking or running data as opposed to not containing running or walking data.

In accordance with certain embodiments, the data may be categorized as either walking or running based entirely on one or two of attribute values. In one embodiment, an attribute may be the trimmed mean of the vector norm (or derivative thereof). In another embodiment, an attribute may relate to an average value of data collected from a plurality of axes (such as the x, y, and/or z axes). In one such embodiment, the attribute may be a median acceleration value associated with a plurality of the axes.

In the example illustrated in FIG. 16, the derivative of the trimmed mean of the vector norm ("der trimmed mean") may be utilized to either classify the data as either walking or running (see, e.g., decisions 1604, 1606, 1616, 1624). In one embodiment, the der trimmed mean may be used as the initial determination distinguishing between walking and running. In certain embodiments, the der trimmed mean alone may determine the classification within either walking or running. For example, if the der trimmed mean falls within a lowest range, then the data may be classified as walking (see, e.g., decision 1606 stemming from not meeting the threshold of decision 1604).

If the der trimmed mean falls within a second range above the lowest range, then further analysis may be performed. In one embodiment, the trimmed mean (as opposed to the derivative of the trimmed mean) may be utilized, whereas data falling below a threshold may be classified as running and data meeting the threshold may be classified as walking (see, e.g., decision, 1612). Further embodiments may employ further ranges of the der. trimmed mean. For example, block 1604 may be utilized to pre-screen data that is above a threshold, such that to create a range that is above the first and/or second ranges. For example, the combination of decisions 1604 and 1616 may be utilized to essentially create two ranges (which may be, for example, a third and fourth range). If the data fails to meet the der trimmed range threshold of decision 1616, further analysis of one or more attributes may be conducted to categorize it as either walking or running. In one embodiment, a determination that the median of the acceleration data associated with all the axes is greater than a first threshold may result in categorizing the data as walking data, yet a negative determination may result in categorizing it as walking data (e.g., determination 1618).

Looking back decision 1616, an affirmative finding may result in creating additional ranges for the der trimmed mean (see e.g., decision 1624; which may be utilized to divide the fourth range into a lower end and an upper end, which may not be equal). Data within the upper end may be categorized as running data, and data in the lower end may be classified upon the same attribute(s) as the data within the third range. In one embodiment, data within the lower end of the fourth range may be categorized based upon the median sensor data associated with one or more sensors along multiple axes. In one embodiment, if the median acceleration value of data associated with all the 3 axes are above a threshold, then the data may be deemed walking, whereas data not meeting the threshold may be deemed running.

Figure 17A:
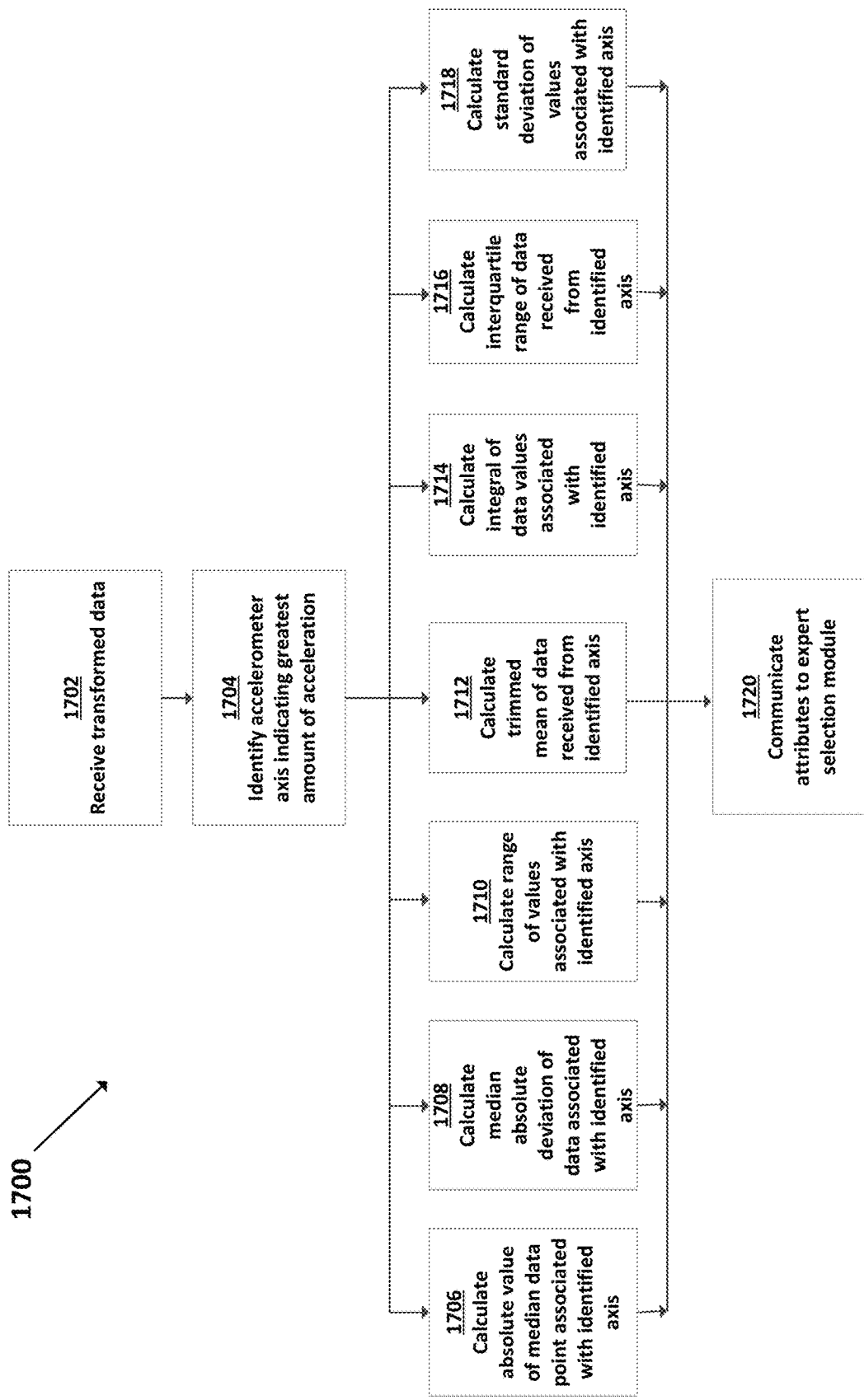
FIGS. 17A-17E show flowchart diagrams that may be implemented to calculate attributes from transformed sensor data in accordance with one embodiment.

FIGS. 17A-17E comprise elements similar to those depicted in FIGS. 9A-9E, and including further details related to one or more attributes calculated from received sensor data. In one example, FIG. 17A depicts an exemplary flowchart 1700 that may include one or more processes for calculation of one or more attributes from received sensor data. In one example, data received from one or more sensors may be validated, and transformed prior to receipt by block 1702. In another example, however, one or more data points may be communicated directly to block 1702 without validation or transformation, and the like.

In one example, FIG. 17A may represent one or more processes to calculate one or more attributes from one or more received accelerometer data points. For example, block 1704 of flowchart 1700 may execute one or more processes to identify an accelerometer axis indicating a greatest amount of acceleration. In one example, and as a result of one or more sorting processes executed at block 806 of flowchart 800, the axis corresponding to a greatest amount of acceleration will be an x-axis, and the like. Accordingly, block 1704 may identify those data values associated with an x-axis. However, those of ordinary skill in the art will understand that the acceleration values associated with highest acceleration may be re-ordered using one or more alternative methods, and such that an axis representing a highest amend of acceleration may differ between data points, or may be re-ordered to be a y-axis or a z-axis, and the like.

As previously described, an attribute may generally be a calculated value representing one or more motions of a user, or parts thereof, and which may be used to subsequently predict an output from a model. Furthermore, a model may be used to, among others, predict oxygen consumption by a user during an activity, and the like. A plurality of different attributes may be calculated from a single data point received from a sensor, or a group of data points/group of samples, otherwise referred to as a dataset, and the like. In one example, a group of attributes used to estimate, among others oxygen consumption by a user may include, a vector normal oven acceleration data point, a derivative of vector normal of an acceleration data point, and/or a Fast Fourier Transform of vector normal of an acceleration data point, as described in relation to FIG. 8A. In another example, an attribute may be calculated as an omnidirectional attribute, wherein an omnidirectional attribute is representative of a motion of a user captured using a sensor sensitive in three dimensions, and the like. In one example, an omnidirectional attribute may be calculated using an accelerometer sensitive to acceleration along an x-axis, y-axis, and z-axis, and the like. In yet another example, an attribute may be calculated as a unidirectional attribute. Accordingly, a unidirectional attribute may be calculated from data outputted from a sensor that is sensitive in a single dimension, and/or to a single variable. In one example, such a sensor may be a heart rate sensor that is sensitive to a heart rate of a user, and the like. In one configuration, one or more attributes may be grouped based on said attributes representing variation in sensor data. In yet another configuration, attributes may be calculated and classified based on a combination of sensor data and biographic information of a user. Biographic information may include, among others, a sex, a mass, and/or a height of a user, and the like.

In another example, further specific attributes may be calculated from data received from an accelerometer. For example, one attribute may be a calculated absolute value of a median data point associated with the axis indicating the greatest amount of acceleration from an accelerometer, and as outlined in relation to exemplary block 1706. In another example, an attribute may include a calculation of a median absolute deviation of data associated with an axis indicating a greatest amount of acceleration from accelerometer, and as described in relation to block 1708. In a further example, block 1710 is an exemplary attribute calculation of a range of values associated with the axis indicating the greatest amount of acceleration from accelerometer. Block 1712 calculates a trimmed mean attributes from the data received from the axis indicating the greatest amount of acceleration from accelerometer. Block 1714 is an example of an attribute calculation of an integral of data values associated with that axis indicating a greatest amount of acceleration from accelerometer. Block 1716 depicts an example process for calculating an interquartile range attribute from data received from said axis indicating the greatest amount of acceleration from accelerometer. Block 1718 calculates a standard deviation attribute of those data values associated with the axis indicating a greatest amount of acceleration.

Block 1720 represents one or more processes to communicate one or more attributes to an expert selection module. Accordingly, an expert selection module may comprise one or more processes to compare one or more calculated attributes to one or more expert models, wherein an expert model may be used to predict/estimates an output associated with an activity being performed by a user. In one example, such an output may be a volume of oxygen consumption by a user, and the like.

Figure 17B:
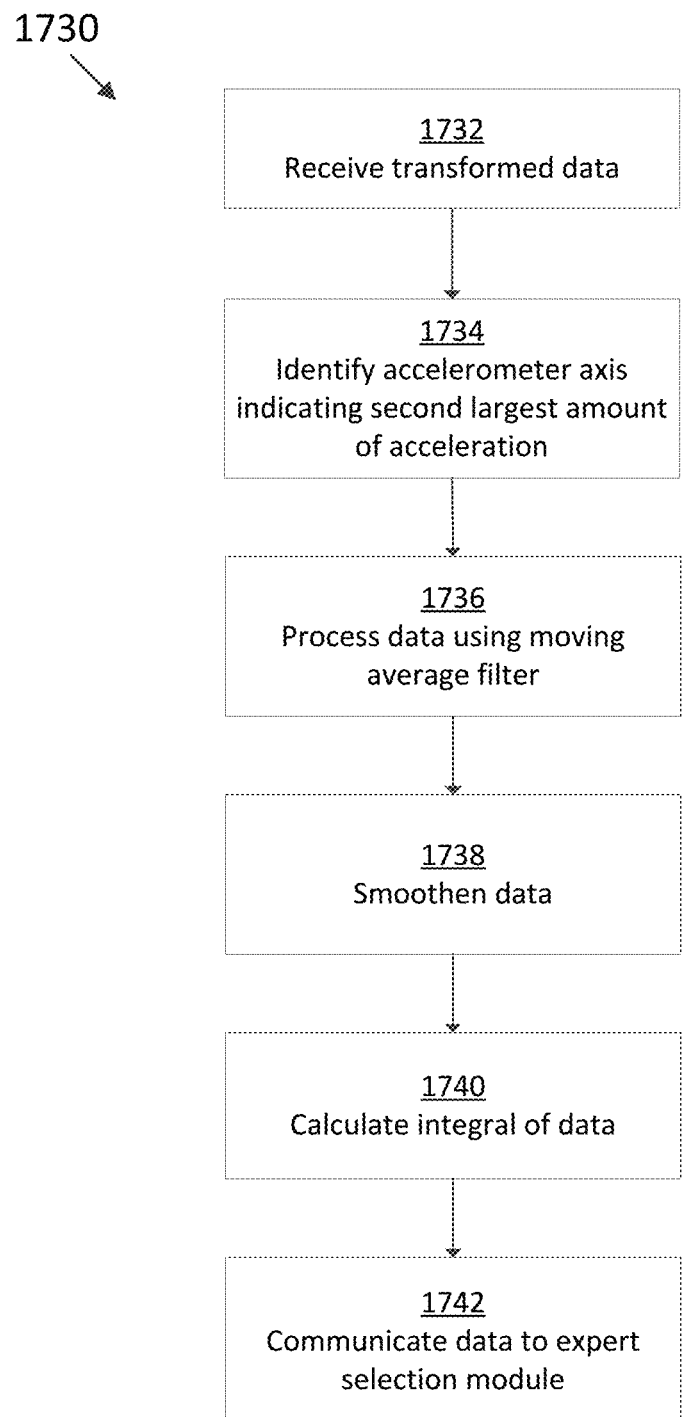

FIG. 17B includes a flowchart 1730, wherein flowchart 1730 may include one or more processes to calculate one or more attributes from received sensor data. Similar to FIG. 17A block 1732 of flowchart 1730 represents one or more processes to receive transformed sensor data. Data transformation is described in further detail in relation to FIG. 8A and FIG. 8B.

Block 1734 of flowchart 1730 may identify accelerometer axis indicating a second largest amount of acceleration. In one example, and subsequent to one or more transformation processes including one or more axis re-ordering processes, the axis indicating a second largest amount of acceleration may be a y-axis, and the like.

Block 1736 may represent one or more processes to filter received data using a moving average filter. Accordingly, a moving average filter may smooth data by replacing data points with the average of neighboring data points within a group of data points. In one example, a moving average filter may be equivalent to a low pass filter, and the like. Those of ordinary skill in the art will recognize several implementations of moving average filters that may be utilized in this example implementation. For example, one or more moving average filters may be implemented within a numerical computing environment, and the like.

Furthermore, and as described in relation to block 1738, one or more processes may be executed to smoothen received data. In one implementation, one or more processes to smoothen received data may also utilize a moving average filter. Accordingly, smoothening may also be accomplished using one or more functions associated with a numerical computing environment.

In one implementation, block 1740 may calculate an attribute of received data as an integral of those data points associated with the axis of accelerometer indicating a second largest amount of acceleration, and the like. Subsequently, the calculated attribute may be communicated to an expert selection module, as described in relation to block 142.

Figure 17C:
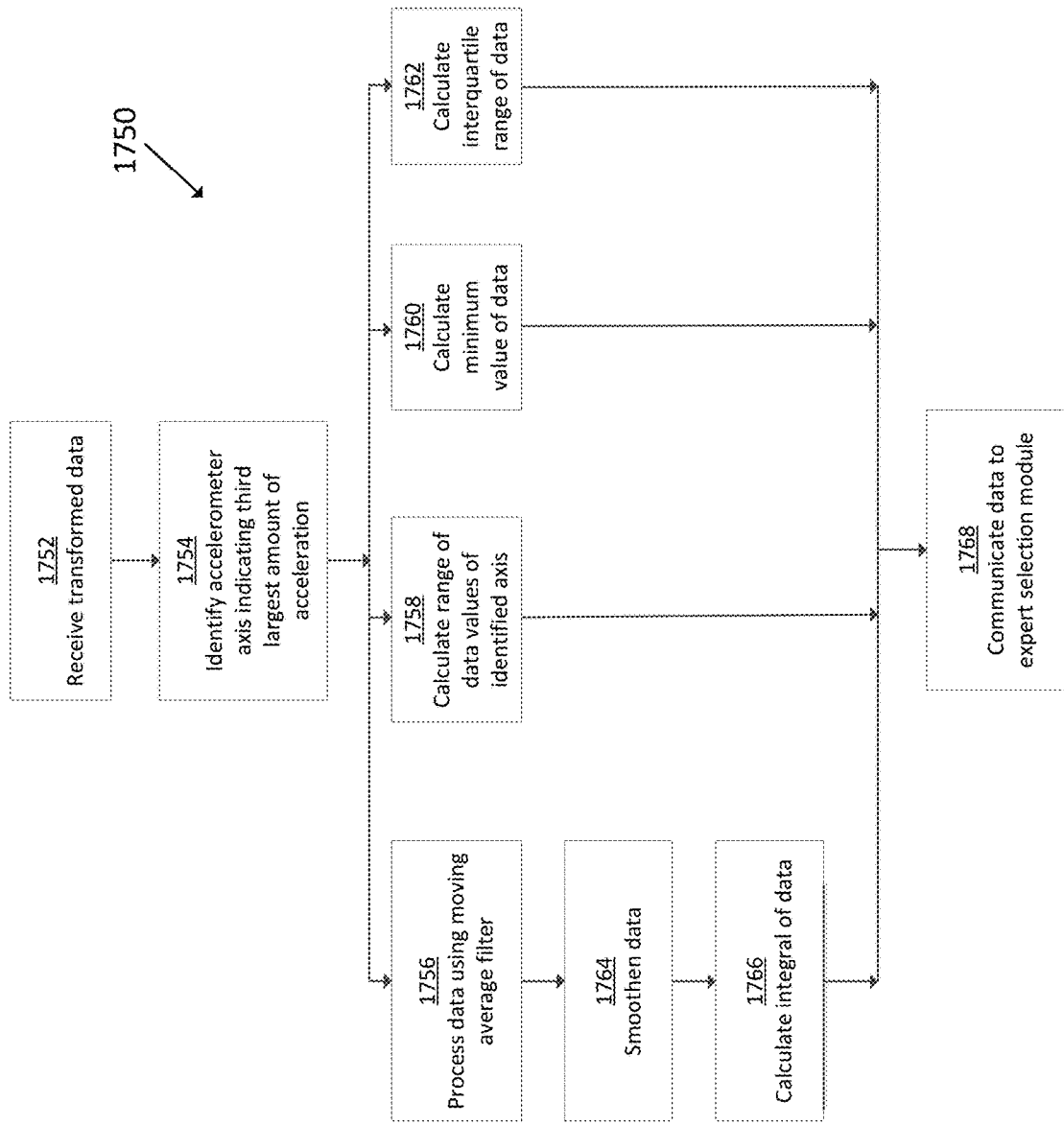

FIG. 17C depicts a flowchart 1750 which may include one or more processes for calculating one or more attributes of received data, wherein the received data may be one or more data points from an accelerometer, and the like. Accordingly, block 1752 represents one or more processes to receive transformed data, wherein data transformations are described in relation to FIG. 8A and FIG. 8B. Alternatively, those of ordinary skill will recognize that the received data may not be transformed, such that received data at block 1752 may, alternatively, be raw data received from one or more sensors.

Block 1754 may represent one or more processes to identify data associated with an axis of accelerometer indicating a third largest amount of acceleration. In one example, and as described in relation to block 806 of FIG. 8A, the axis associated with a third largest amount of acceleration may be a z-axis.

Block 1756 of flowchart 1750 represents one or more processes to filter received data using a moving average filter. Those of ordinary skill in the art will recognize that various moving average filter processes that may be used to filter the received data using, among others, a numerical computing environment, and the like. Block 1764 may represent one or more processes to smoothen received data. For example, a numerical computing environment may include one or more smoothening functions and/or processes, wherein said smoothening functions will be readily understood to those of skill in the art. Furthermore, moving average filters and smoothening processes are described in relation to blocks 1736 and 1738 from FIG. 17. Block 1766 calculates an attribute associated with an integral of the received data.

Block 1758 of flowchart 1750 may represent one or more processes for calculating an attribute representing a range of data values associated with the axis for presenting a third largest amount of acceleration from an accelerometer. Additionally or alternatively, block 1760 may execute one or more processes to calculate a minimum value attribute associated with those data points indicating a third largest amount of acceleration from an accelerometer. Block 1762 represents one or more processes to calculate an interquartile range of data associated with that axis indicating a third largest amount of acceleration associated with an accelerometer, and the like.

Block 1768 communicates one or more attributes to an expert selection module, wherein said expert selection module is described in relation to FIG. 14.

Figure 17D:
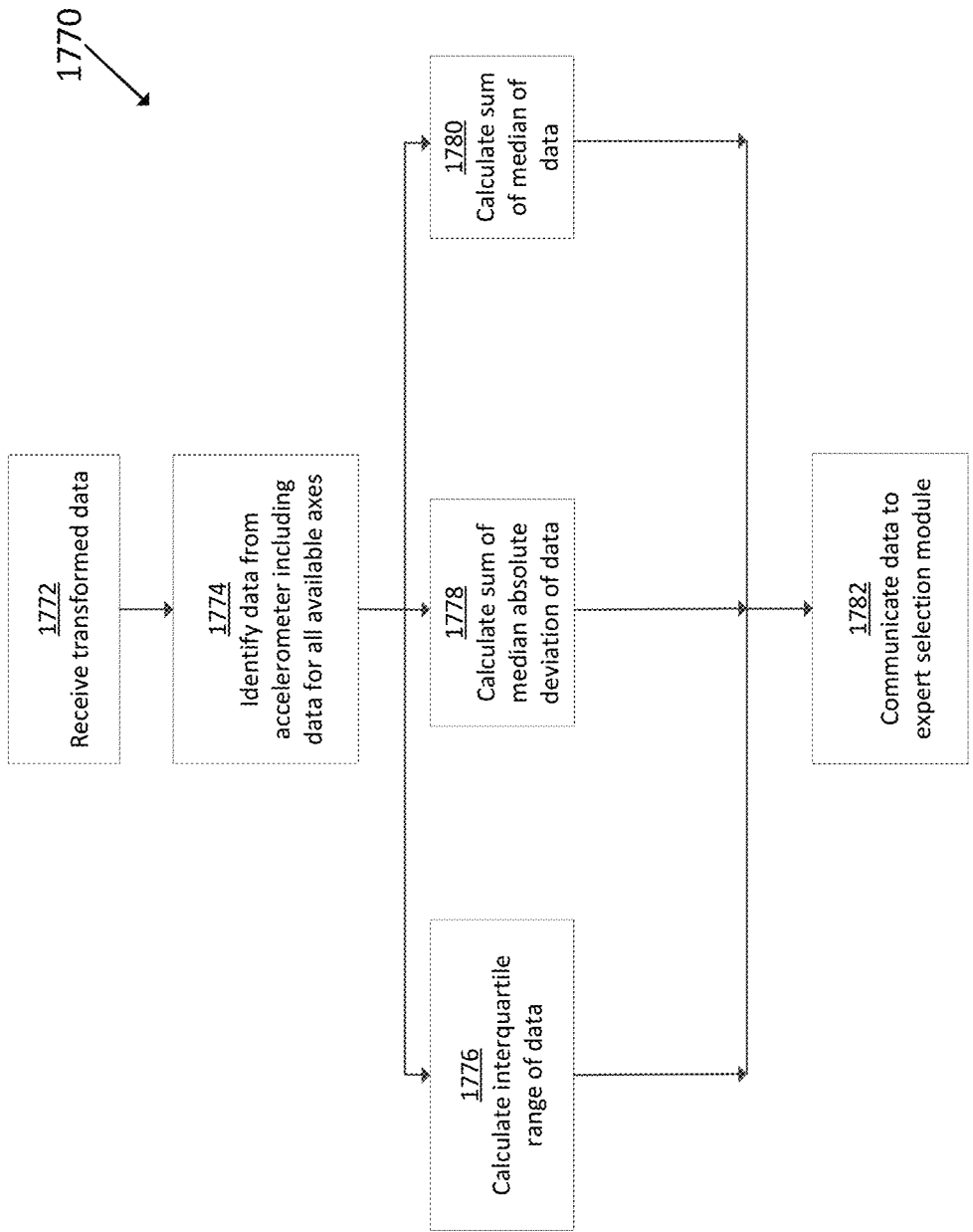

FIG. 17D is a flowchart diagram 1770 which may represent one or more processes to calculate one or more attributes associated with received sensor data. For example, block 1772 may receive transformed sensor data from accelerometer. Accordingly, block 1774 may group those data points from all axes associated with the accelerometer. In one example, an accelerometer may output data related to one, two, or three orthogonal axes (x-axis, y-axis, and/or z-axis). Block 1776 represents one or more processes to calculate an interquartile range attribute of the data associated with all available axes. Furthermore, block 1778 represents those processes for calculation of a sum of median absolute deviation of the data associated with all available axes. Additionally, block 1780 calculates a sum of median data attribute associated with those data points from all available axes from the accelerometer.

Subsequent to calculation of one or more attributes, and as represented by block 1782 of flowchart 1770, one or more attributes may be communicated to an expert selection module. An expert selection module may be one or more processes associated with selecting a best-fit model associated with calculated attributes, and as described in further detail in relation to FIG. 14.

Figure 17E:
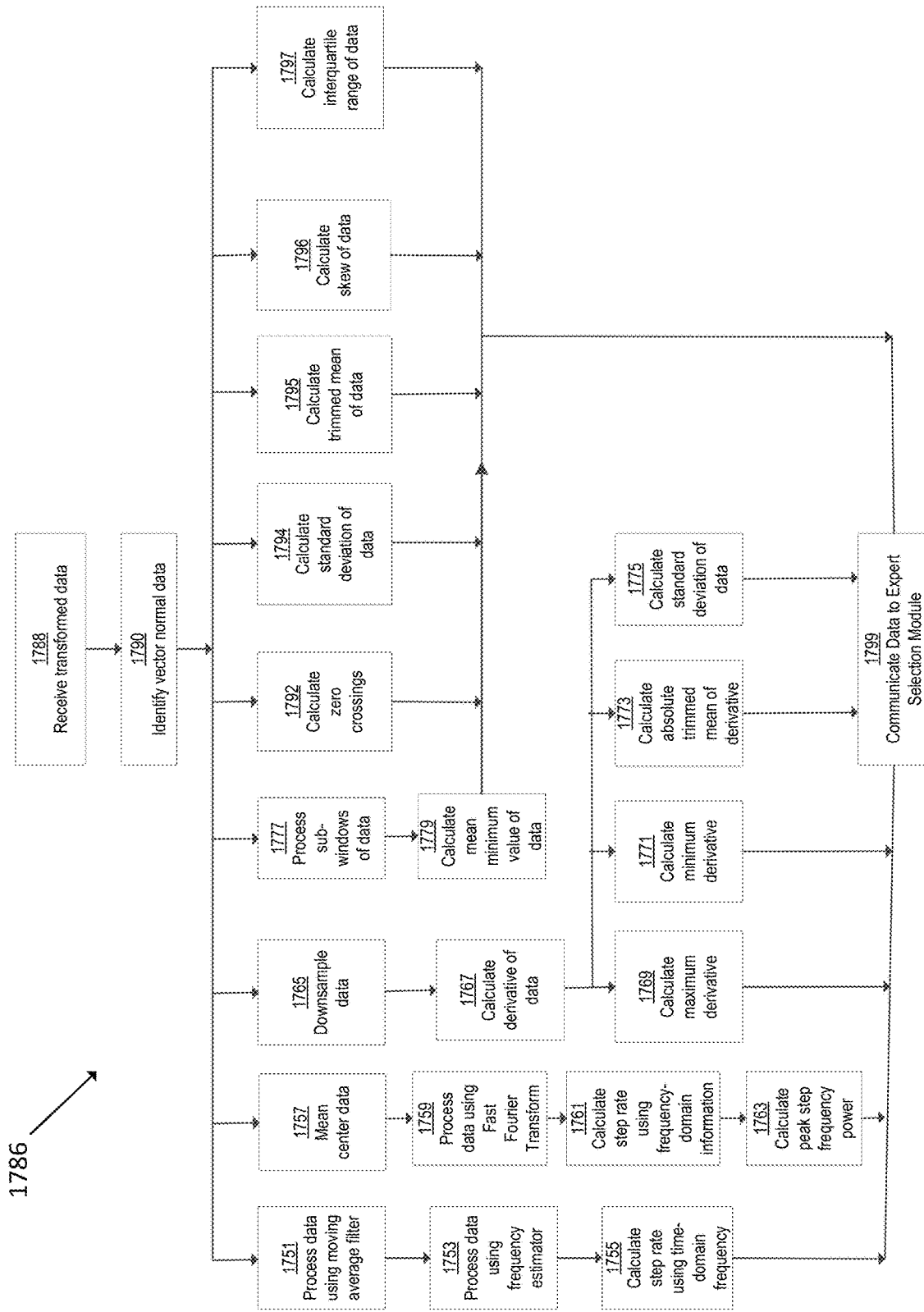

FIG. 17E is a flowchart diagram representing one or more processes to calculate attributes associated with received sensor data. In one example, flowchart 1786 represents one or more attribute calculation processes associated with data received from an accelerometer, and the like. Accordingly, block 1788 represents one or more processes to receive transformed accelerometer data. In one implementation, and as described in relation to FIG. 8A, accelerometer data may be transformed by calculation of a vector normal of said data, and the like. In one example, block 1790 identifies a calculated vector normal of accelerometer data. From said calculated vector normal data, one or more attributes may be identified.

In one example, block 1751 processes vector normal data using a moving average filter. As previously described, those of ordinary skill in the art will recognize various implementations of moving average filters which may be utilized in the following disclosure. Subsequently, and as described in relation to block 1753, the filtered data may be processed using a frequency estimator. Similarly, those of ordinary skill in the art will recognize various frequency estimator functions/processes that may be utilized in relation to block 1753. Block 1755 represents one or more processes to calculate a step rate attribute using a time-domain frequency, and from received accelerometer data.

Block 1757 represents one or more processes to mean-center received vector normal data. Subsequently, and as described in relation to block 1759, the mean-centered data may be transformed using a Fast Fourier Transform. Those of ordinary skill in the art once again will recognize one or more processes for carrying out a Fast Fourier Transform. Block 1761 represents one or more processes to calculate a step rate using frequency-domain information found from the Fast Fourier Transform. Subsequently, block 1763 calculates a peek step frequency power attribute.

Block 1765 may be executed to downsample the received vector normal data. Those of ordinary skill in the art will recognize various downsampling processes that may be utilized in relation to block 1765. Subsequently, block 1767 may be executed to calculate a derivative of the downsampled data. Alternatively, and using the calculated derivative of the data from block 1767, a minimum and derivative attribute may be calculated at block 1771, an absolute trimmed mean of a derivative attribute may be calculated at block 1773, and/or a standard deviation of data may be calculated at block 1775, and the like.

Block 1777 represents one or more processes to process sub-windows of data. As previously described, a window of data may be a duration of time measuring, among others, 5.12 seconds in length, and sampling data at a rate of 25 Hz, thereby producing 128 accelerometer samples, and the like. A sub-window of data may be, among others, a fraction of a full window. For example, a sub-window may be one quarter of a full window. As such, a sub window may include 128/4=32 data samples, and the like. Block 1779 of flowchart 1786 represents one or more processes to calculate a mean a value of the data from block 1777, wherein said calculation represents an attribute of the received vector normal data, and the like.

Block 1792 calculates one or more zero crossings of the received vector normal data. Those of ordinary skill in the art will recognize one or more processes for identifying and/or calculating zero crossings, and the like. As such, the calculation of one or more zero crossings at block 1792 represents an attribute of the received data.

Block 1794 represents one or more processes that may be used to calculate a standard deviation of received vector normal data, wherein said standard deviation represents another attribute of the received data. Similarly, block 1795 represents a calculation of an attribute of the received data by executing one or more processes to calculate a trimmed mean of the received data, and the like. In a similar manner to those one or more attributes previously described, a trimmed mean will be readily understood to those of ordinary skill in the art, and wherein, in one implementation, a trimmed mean is a mean that excludes outliers from a data set.

Block 1796 may execute one or more processes to calculate a skew attribute of received vector normal data. A skew will be readily understood to those of ordinary skill with knowledge of statistics, and wherein a skew may be a measure of an extent to which a probability distribution is biased, and the like.

Block 1797 may represent one or more processes to calculate an interquartile range attribute of the received vector normal data. Accordingly, those of ordinary skill in the art will understand one or more processes for calculation of an interquartile range associated with statistical analysis of data, and the like.

In one example, and for accelerometer data having data output associated with three mutually orthogonal axes (x-axis, y-axis, and z-axis), those attributes calculation may include, in addition to those described in relation to FIGS. 17A-17E: A range of x-axis values (x_range), an arm swing frequency (in one implementation, associated with the motion of an appendage of a user) (L_peak_freqA), a trimmed mean of x-axis values (X_trimmed_mean), an interquartile range of z-axis values (Z_iqRange), an arm swing power (in one implementation, associated with motion of an appendage of a user) (L_peak_powA), a difference in a number of vector normal values above or below a mean, otherwise referred to as a skew (Skew), an integral of x-axis values (X_integral), a step frequency determined from a vector normal, and not using Fast Fourier Transform (TimeDomainFrequency), a summation of max of quartered windows (wherein a window may be a period of time for which sensor data is outputted from a sensor device) (Sum_max), a standard deviation of a derivative (Der_std), a sum of the standard deviation of x-, y-, and z-axis values (AS_sum_std), an integral of a vector normal (Integral), a step frequency power (H_peak_powA), a mean of the standard deviation values of quartered windows (Mean_std), a maximum of a vector normal (Max), a median absolute deviation of the derivative of the vector normal (Der_med_abs_dev), an interquartile range of x-axis values (X_iqRange), a trimmed mean of vector normal (Trimmed_mean), and/or a standard deviation of x-axis values (X_std-dev), among others.

CONCLUSION

Providing an activity environment having one or more of the features described herein may provide a user with an experience that will encourage and motivate the user to engage in athletic activities and improve his or her fitness. Users may further communicate through social communities and challenge one another to participate in point challenges.

Aspects of the embodiments have been described in terms of illustrative embodiments thereof. Numerous other embodiments, modifications and variations within the scope and spirit of the appended Clauses will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

We claim:

1. A non-transitory computer-readable medium comprising computer-executable instructions that when executed by a processor, perform at least:
   generating a plurality of activity models using historical training data associated with a plurality of activities;
   receiving, from an accelerometer device and via one or more wireless networks, motion data comprising one or more data points as a result of motion of a user;
   calculating, in-real time and as the motion data is received from the accelerometer device, a first one or more attributes for the motion data;
   determining, for each activity model of the plurality of activity models, a probability that that activity model provides, from the plurality of activity models, a most accurate estimation of a second motion metric by comparing the first one or more attributes to second one or more attributes of that activity model;

selecting, based on results of the comparing, a first model, from the plurality of activity models, as a best-match to the first one or more attributes, wherein the first model is selected as the best-match based on a determination that the first model is associated with a highest probability of each of the probabilities;

calculating, using the first model, the second motion metric for the user, wherein the calculating comprises inputting the first one or more attributes into the first model and receiving an output comprising the second motion metric from the first model;

calculating, using the second motion metric for the user, an energy expenditure associated with a motion of the user; and sending, to a display screen of a user device and via the one or more wireless networks, the energy expenditure.

2. The non-transitory computer-readable medium of claim 1, wherein the plurality of activity models comprise motion data from a plurality of individuals.

3. The non-transitory computer-readable medium of claim 1, wherein the non-transitory computer-readable medium further comprises computer-executable instructions that when executed by a processor, perform at least:
identifying from the motion data a first accelerometer axis having a first greatest amount of acceleration for a first time period; and
based upon the identification of the first accelerometer axis, calculating a first attribute for the motion data along the first accelerometer axis.

4. The non-transitory computer-readable medium of claim 3, wherein the first accelerometer axis is one of an x-axis, a y-axis and a z-axis and the first attribute selected from a group consisting of: a vector normal calculated as a square root of a sum of squares of x-axis, y-axis, and z-axis values; a range of x-axis values; an arm swing frequency; a trimmed mean of x-axis values; an interquartile range of z-axis values; an arm swing power; a skew; an integral of x-axis values; a step frequency determined from a vector normal using a time domain frequency; a summation of max of quartered windows; a standard deviation of a derivative; a sum of a standard deviation of x-axis, y-axis, and z-axis values; an integral of a vector normal; a step frequency power; a mean of a standard deviation values of quartered windows; a maximum of a vector normal; a median absolute deviation of a derivative of a vector normal; an interquartile range of x-axis values; a trimmed mean of a vector normal; an absolute value of a median data point of x-axis data; a median absolute deviation of data associated with x-axis; a standard deviation of x-axis data; an integral of y-axis values; an integral of z-axis data; a range of z-axis data; a minimum value of z-axis data; an interquartile range of data from the x-axis, y-axis, and z-axis; a sum of a median absolute deviation of data from the x-axis, y-axis, and z-axis; a sum of a median of data from x-axis, y-axis, and z-axis; a maximum derivative of a vector normal; a minimum derivative of a vector normal; an absolute trimmer mean of a derivative of a vector normal; a standard deviation of a vector normal; one or more zero crossings of vector normal data; a skew of vector normal data; an interquartile range of vector normal data; and a standard deviation of x-axis values.

5. The non-transitory computer-readable medium of claim 1, wherein the non-transitory computer-readable medium further comprises computer-executable instructions that when executed by a processor, perform at least:
validating at least a portion of the one or more data points by comparison to one or more threshold values.

6. The non-transitory computer-readable medium of claim 5, wherein one or more of the attributes are calculated from a combination of the one or more data points and biographic data related to the user.

7. The non-transitory computer-readable medium of claim 6, wherein the biographic data includes data relating to at least: a sex, a mass, and a height of the user.

8. The non-transitory computer-readable medium of claim 1, wherein the motion data is captured while the accelerometer device is worn on an appendage of the user.

9. The non-transitory computer-readable medium of claim 1, wherein the motion data comprises one or more of historical motion data or real-time motion data, and wherein the accelerometer device comprises a body-worn device.

10. A method, comprising:
generating a plurality of activity models using historical training data associated with a plurality of activities;
receiving, from an accelerometer device and via one or more wireless networks, motion data comprising one or more data points as a result of motion of a user;
calculating, in-real time and as the motion data is received from the accelerometer device,
a first one or more attributes for the motion data;
determining, for each activity model of the plurality of activity models, a probability that that activity model provides, from the plurality of activity models, a most accurate estimation of a second motion metric by comparing the first one or more attributes to second one or more attributes of that activity model;
selecting a first model from the plurality of activity models based on the comparing, wherein the first model is selected based on a determination that the first model is associated with a highest probability of each of the probabilities;
calculating, using the first model, the second motion metric for the user, wherein the calculating comprises inputting the first one or more attributes into the first model and receiving an output comprising the second motion metric from the first model;
calculating, using the second motion metric for the user, an energy expenditure associated with a motion of the user; and
sending, to a display screen of a user device and via the one or more wireless networks, the energy expenditure.

11. The method of claim 10, wherein the first model is selected based on determining that attributes of the first model are a best-match to one or more attributes of the motion data.

12. The method of claim 10, further comprising:
identifying from the motion data a first accelerometer axis having a first greatest amount of acceleration for a first time period; and
based upon the identification of the first accelerometer axis, calculating a first attribute for the motion data along the first accelerometer axis.

13. The method of claim 12, wherein the first accelerometer axis is one of an x-axis, a y-axis and a z-axis and the first attribute selected from a group consisting of: a vector normal calculated as a square root of a sum of squares of x-axis, y-axis, and z-axis values; a range of x-axis values; an arm swing frequency; a trimmed mean of x-axis values; an interquartile range of z-axis values; an arm swing power; a skew; an integral of x-axis values; a step frequency determined from a vector normal using a time domain frequency; a summation of max of quartered windows; a standard deviation of a derivative; a sum of a standard deviation of x-axis, y-axis, and z-axis values; an integral of a vector normal; a step frequency power; a mean of a standard deviation values of quartered windows; a maximum of a vector normal; a median absolute deviation of a derivative of a vector normal; an interquartile range of x-axis values; a trimmed mean of a vector normal; an absolute value of a median data point of x-axis data; a median absolute deviation of data associated with x-axis; a standard deviation of x-axis data; an integral of y-axis values; an integral of z-axis data; a range of z-axis data; a minimum value of z-axis data; an interquartile range of data from the x-axis, y-axis, and z-axis; a sum of a median absolute deviation of data from the x-axis, y-axis, and z-axis; a sum of a median of data from x-axis, y-axis, and z-axis; a maximum derivative of a vector normal; a minimum derivative of a vector normal; an absolute trimmer mean of a derivative of a vector normal; a standard deviation of a vector normal; one or more zero crossings of vector normal data; a skew of vector normal data; an interquartile range of vector normal data; and a standard deviation of x-axis values.

14. The method of claim 10, further comprising:
validating at least a portion of the data points by comparison to one or more threshold values.

15. The method of claim 10, wherein one or more of the attributes are calculated from a combination of one or more data points captured from the accelerometer device and biographic data related to the user.

16. The method of claim 15, wherein the biographic data includes data relating to at least: a sex, a mass, and a height of the user.

17. The method of claim 10, wherein the motion data is captured while the acceleration device is worn on an appendage of the user.

18. An apparatus comprising:
one or more processors; and
memory storing computer-readable instructions that, when executed by the one or more processors, cause the apparatus to:
generate a plurality of activity models using historical training data associated with a plurality of activities;
receive, from an accelerometer device and via one or more wireless networks, motion data comprising one or more data points as a result of motion of a user;
calculate, in-real time and as the motion data is received from the accelerometer device, a first one or more attributes for the motion data;
determine, for each activity model of the plurality of activity models, a probability that that activity model provides, from the plurality of activity models, a most accurate estimation of a second motion metric by comparing the first one or more attributes to second one or more attributes of that activity model;
select a first model from the plurality of activity models based on the comparing, wherein the first model is selected based on a determination that the first model is associated with a highest probability of each of the probabilities;
calculate, using the first model, the second motion metric for the user, wherein the calculating comprises inputting the first one or more attributes into the first model and receiving an output comprising the second motion metric from the first model;
calculate, using the second motion metric for the user, an energy expenditure associated with the motion of the user; and
transmit, to a user device and via the one or more wireless networks, the energy expenditure.

19. The apparatus of claim 18, the memory storing computer-readable instructions that, when executed by the one or more processors, cause the apparatus to:
receive heart rate data obtained from the user by the accelerometer during performance of the motion; and
determine to cease utilizing heart rate data based upon the accelerometer device providing data indicative that the user has reduced their physical activity below a threshold amount for at least a first time frame.

20. The apparatus of claim 18, wherein the motion data is captured while the accelerometer device is worn on an appendage of the user.

21. The apparatus of claim 18, wherein the motion data is captured while the accelerometer device is worn in proximity to a waist of the user.

* * * * *